(12) United States Patent
Miyamoto et al.

(10) Patent No.: US 8,939,998 B2
(45) Date of Patent: Jan. 27, 2015

(54) MEDICAL SUTURE AND LIGATURE INSTRUMENT AND MEDICAL SUTURE AND LIGATURE TOOL

(75) Inventors: Satoshi Miyamoto, Tokyo (JP); Norio Onishi, Tokyo (JP)

(73) Assignee: Olympus Corporation (JP)

( * ) Notice: Subject to any disclaimer, the term of this patent is extended or adjusted under 35 U.S.C. 154(b) by 2180 days.

(21) Appl. No.: 11/815,247

(22) PCT Filed: Jan. 31, 2006

(86) PCT No.: PCT/JP2006/301569
§ 371 (c)(1),
(2), (4) Date: May 18, 2009

(87) PCT Pub. No.: WO2006/082811
PCT Pub. Date: Aug. 10, 2006

(65) Prior Publication Data
US 2010/0049218 A1 Feb. 25, 2010

(30) Foreign Application Priority Data

Feb. 4, 2005 (JP) ................................. 2005-028677

(51) Int. Cl.
*A61B 17/04* (2006.01)
*A61B 17/12* (2006.01)
*A61B 17/06* (2006.01)

(52) U.S. Cl.
CPC ....... *A61B 17/12013* (2013.01); *A61B 17/0401* (2013.01); *A61B 17/0482* (2013.01);
(Continued)

(58) Field of Classification Search
USPC .................................. 606/139, 144–148, 232
See application file for complete search history.

(56) References Cited

U.S. PATENT DOCUMENTS 5,281,238 A * 1/1994 Chin et al. .................... 606/148
5,336,229 A * 8/1994 Noda ............................ 606/144
(Continued)

FOREIGN PATENT DOCUMENTS

EP        1 685 802        8/2006
JP       2001-000440       1/2001
(Continued)

OTHER PUBLICATIONS

PCT International Search Report and Written Opinion dated Apr. 18, 2006 issued in corresponding PCT International Application No. PCT/JP2006/301569.
(Continued)

*Primary Examiner* — Dianne Dornbusch
*Assistant Examiner* — Alexander Orkin
(74) *Attorney, Agent, or Firm* — Ostrolenk Faber LLP

(57) ABSTRACT

A biological tissue is sutured or ligatured, a suture and ligature member such as a ligature wire is cut, and then a holding member is reliably recovered from the body. In a holding member of a medical ligature tool, a protrusion is disposed between distal lateral holes, and proximal lateral holes, so that it protrudes outward in a diameter direction thereof. On the other hand, a concave portion is formed in the inner periphery of a cutting member. When the cutting member is extended to cut a ligature wire, the concave portion is fitted to the protrusion to allow the holding member to engage the cutting member.

13 Claims, 18 Drawing Sheets

(52) U.S. Cl.
CPC ......... *A61B 17/0487* (2013.01); *A61B 17/0467* (2013.01); *A61B 2017/0417* (2013.01); *A61B 2017/0445* (2013.01); *A61B 2017/0458* (2013.01); *A61B 2017/0464* (2013.01); *A61B 2017/0488* (2013.01); *A61B 2017/0496* (2013.01); *A61B 2017/06052* (2013.01)
USPC .......................................... 606/144; 606/139

(56) References Cited

U.S. PATENT DOCUMENTS

| | | | | |
|---|---|---|---|---|
| 5,336,231 | A | * | 8/1994 | Adair ............................. 606/148 |
| 5,383,905 | A | * | 1/1995 | Golds et al. ................... 606/232 |
| 5,405,351 | A | | 4/1995 | Kinet et al. |
| 5,797,928 | A | * | 8/1998 | Kogasaka ...................... 606/144 |
| 2003/0144673 | A1 | | 7/2003 | Onuki et al. ................... 606/139 |
| 2003/0204205 | A1 | * | 10/2003 | Sauer et al. .................... 606/232 |
| 2003/0236535 | A1 | | 12/2003 | Onuki et al. ................... 606/144 |
| 2004/0181238 | A1 | | 9/2004 | Zarbatany et al. |

FOREIGN PATENT DOCUMENTS

| | | |
|---|---|---|
| JP | 2003-204966 | 7/2003 |
| JP | 2004-601 | 1/2004 |

OTHER PUBLICATIONS

Japanese Office Action mailed Nov. 16, 2010 in connection with corresponding Japanese Patent Application No. 2005-028677.
English translation of Japanese Office Action issued in connection with corresponding Japanese application provided as an explanation of prior art relevancy.
Search Report issued by European Patent Office on Jul. 22, 2013 in connection with corresponding EP application No. EP 06 71 2712.

* cited by examiner

US 8,939,998 B2

MEDICAL SUTURE AND LIGATURE INSTRUMENT AND MEDICAL SUTURE AND LIGATURE TOOL

CROSS REFERENCE TO RELATED APPLICATION

The present application is a 35 U.S.C. §§371 national phase conversion of PCT/JP2006/301569, filed Jan. 31, 2006, which claims priority of Japanese Application No. 2005-028677, filed Feb. 4, 2005, the disclosure of which has been incorporated herein by reference. The PCT International Application was published in the Japanese language.

TECHNICAL FIELD

The present invention relates to a medical suture and ligature instrument and a medical suture and ligature tool which are used along with an endoscope and used for an endoscopic treatment such as suturing and ligaturing a biological tissue in a body.

This application claims the priority of Japanese Patent Application No. 2005-028677, filed on Feb. 4, 2005, the entire contents of which are incorporated herein by reference.

BACKGROUND ART

A medical suture and ligature instrument for suturing or ligaturing a biological tissue in a body while observing the biological tissue by the use of an endoscope is known, which includes a sheath to be inserted through a channel of the endoscope, an operating wire inserted into the sheath to extend and retract, and a medical suture and ligature tool to be locked to a hook at a distal end of the operating wire. The medical ligature tool has a ligature wire of a loop shape and the size of the loop can be adjusted by allowing a stopper to extend and retract along the ligature wire. A folding-back portion to be locked to the hook is formed in the proximal end portion of the ligature wire. At the time of ligaturing a pathological lesion portion, the loop is hooked to the pathological lesion portion, the hook is made to retract, and the diameter of the loop is reduced, thereby binding the pathological lesion portion tight. Thereafter, the ligature wire is cut between the portion binding the pathological lesion portion tight and the folding-back portion and the ligature wire is detained in the body in a state where the biological tissue is bound tight.

Here, a medical ligature tool is also known in which a cutting member is disposed outside of a sheath into which an operating wire is inserted so as to extend and retract and a holding member for receiving the cutting member while holding the ligature wire between a folding-back portion and a stopper is disposed in the medical ligature tool, so as to perform as a series of operations an operation of tightly binding and ligaturing a pathological lesion portion with the medical ligature tool and an operation of separating the medical ligature tool from the operating wire (for example, see Patent Document 1). The holding member has a cylindrical shape through which the ligature wire is inserted and an annular protrusion is incorporated in a substantially central portion in an axial direction thereof. The portions closer to the distal and the proximal ends with respect to the protrusion, each have a hole through which the ligature wire can be inserted. The ligature wire is inserted inside via a distal opening of the passage penetrating the holding member, passes through the distal hole, is drawn along the outer periphery of the protrusion in the longitudinal direction, extends into the holding member through the proximal hole, and then is drawn out of the proximal opening. In such a medical ligature tool, a pathological lesion portion is tightly bound, the cutting member is made to advance, and the ligature wire is cut by interposing the ligature wire between the protrusion and the cutting member. The holding member spontaneously falls off and is discharged after the ligature wire is cut.

[Patent Document 1] Japanese Unexamined Patent Publication No. 2003-204966

DISCLOSURE OF THE INVENTION

Problems that the Invention is to Solve

However, in the conventional medical ligature tool, when the friction between the holding member and the ligature wire is large, the holding member might not spontaneously fall off, that has been interfered other treatments. In this case, it is necessary to grasp the holding member with grasping forceps or the like and to separate the holding member from the ligature wire. In this case, since it is necessary to pull out the medical suture and ligature instrument via a channel of an endoscope and then to insert the endoscopic treatment tool such as grasping forceps instead, there is a problem in that surgical procedure becomes complicated and operation time is prolonged.

The invention is contrived to solve the above-mentioned problem. An object of the invention is to reliably recover the holding member from the body after suturing or ligaturing a biological tissue and cutting a suture and ligature member such as a ligature wire.

Means for Solving the Problems

In order to accomplish the above-mentioned object, according to a first aspect of the present invention, a medical suture and ligature instrument is provided including: an insertion section which has a distal end, a proximal end, and an elongated axis which is inserted into a body; a cutting member which is disposed to be movable relative to the insertion section and which has a cutting edge; a handle operating section which is disposed on the proximal side of the insertion section and which an operator operates; an operation unit which includes the insertion section, the cutting member, and the handle operating section; and a medical suture and ligature tool which is disposed on the distal side of the operation unit and which sutures or ligatures a biological tissue, wherein the medical suture and ligature tool includes: a flexible suture and ligature member; and a holding member which has a holding portion for holding the suture and ligature member in a path along which the cutting member moves so as to cut the suture and ligature member by the use of the cutting member, and wherein the holding member includes an engaging portion which can engage with the operation unit so as to allow the holding member to engage with the operation unit even after the suture and ligature member is cut by the use of the cutting member.

In the medical suture and ligature instrument, when the suture and ligature member is cut with the cutting member, the holding member pressed to the operation unit by the suture and ligature member engages the engaging portion. Accordingly, when the suture and ligature member is removed from the body, the holding member is discharged from the body along with the operation unit.

In the medical suture and ligature instrument according to a second aspect of the present invention, a locking member used for locking the suture and ligature member to a biological tissue may be attached to a distal end of the suture and ligature member of the medical suture and ligature tool and the operation unit may include a medical puncture unit having a tissue puncture member for puncturing the biological tissue along with the locking member.

The medical suture and ligature instrument forms a through-hole in the biological tissue by puncturing the biological tissue with a tissue puncturing member and allows the suture and ligature member to pass through the biological tissue by allowing the suture and ligature member to pass through the through-hole. Thereafter, the pathological lesion portion is sutured by fastening the biological tissue by the use of the suture and ligature member.

In the medical suture and ligature instrument according to a third aspect of the present invention, the holding member may be provided with a lateral hole for drawing the suture and ligature member into the inside of the holding member from the outside thereof and the engaging portion is disposed so that the cutting member is located closer to the distal end than the lateral hole.

In the medical suture and ligature instrument, when the cutting member is made to extend, the suture and ligature member drawn out of the holding member is first cut with the cutting edge and the engaging portion then engages, thereby allowing the holding member to engage the cutting member.

In the medical suture and ligature instrument according to a fourth aspect of the present invention, the cutting member may have a cutting edge at the distal end thereof and the holding member may be provided with the engaging portion at a position not interfering with the cutting edge.

In the medical suture and ligature instrument, since the cutting end does not interfere with the engaging portion of the holding member side, the movement of the cutting edge is not hindered by the engaging portion and thus it is easy to cut the suture and ligature member.

According to a fifth aspect of the present invention, a medical suture and ligature tool is provided including: a flexible suture and ligature member which sutures or ligatures a biological tissue; and a holding member having a holding portion for holding the suture and ligature member in a path along which a cutting member for cutting the suture and ligature member moves, wherein the holding member includes an engaging portion which can engage with the operation unit so as to allow the holding member to engage with the operation unit even after the suture and ligature member is cut via the use of the cutting member.

In the medical suture and ligature tool, by allowing the holding member to engage with the cutting member by the use of the engaging portion of the holding member, it is possible to maintain a state where the holding member is fitted to the operation unit even after the suture and ligature member drawn to the outer periphery of the holding member is cut via the cutting member.

Advantages of the Invention

According to the present invention, since the holding member is configured to engage the operation unit side, it is possible to maintain a state where the holding member is fitted to the operation unit side even after the suture and ligature member drawn to the outer periphery of the holding member is cut with the cutting member. Accordingly, it is possible to reliably remove the holding member from the body without inserting other treatment instruments. When the cutting member and the holding member are configured to engage each other, the operation of cutting the suture and ligature member and the operation of allowing the holding member to engage can be carried out as a series of operations, thereby facilitating surgical procedure.

DESCRIPTION OF REFERENCE NUMERALS AND SIGNS

1: MEDICAL SUTURE AND LIGATURE INSTRUMENT
2: MEDICAL LIGATURE TOOL (MEDICAL SUTURE AND LIGATURE TOOL)
3: OPERATION UNIT
4: INSERTION SECTION

10: CUTTING MEMBER
12: HANDLE OPERATING SECTION
20: LIGATURE WIRE (SUTURE AND LIGATURE MEMBER)
22: STOPPER (FIXING MEMBER)
23, 40, 50, 60, 70, 80, 103: HOLDING MEMBER
30, 43, 64: CONCAVE PORTION (ENGAGING PORTION)
35, 41, 61: PROTRUSION (ENGAGING PORTION, HOLDING-SIDE ENGAGING PORTION)
33a, 33b: DISTAL LATERAL HOLE (LATERAL HOLE)
34a, 34b: PROXIMAL LATERAL HOLE (LATERAL HOLE)
51: TAPERED PORTION (ENGAGING PORTION, HOLDING-SIDE ENGAGING PORTION)
71, 81: CONCAVE PORTION (ENGAGING PORTION, HOLDING-SIDE ENGAGING PORTION)
73: PROTRUSION (ENGAGING PORTION)
92: MEDICAL SUTURE TOOL (MEDICAL SUTURE AND LIGATURE TOOL)
W1: PATHOLOGICAL LESION PORTION (BIOLOGICAL TISSUE)
W2, W3: BIOLOGICAL TISSUE

BEST MODE FOR CARRYING OUT THE INVENTION

Preferred embodiments of the invention will be described in detail with reference to the drawings. However, the invention is not limited to the following embodiments, but, for example, elements of the embodiments may be properly combined.

First Embodiment

Figure 1:
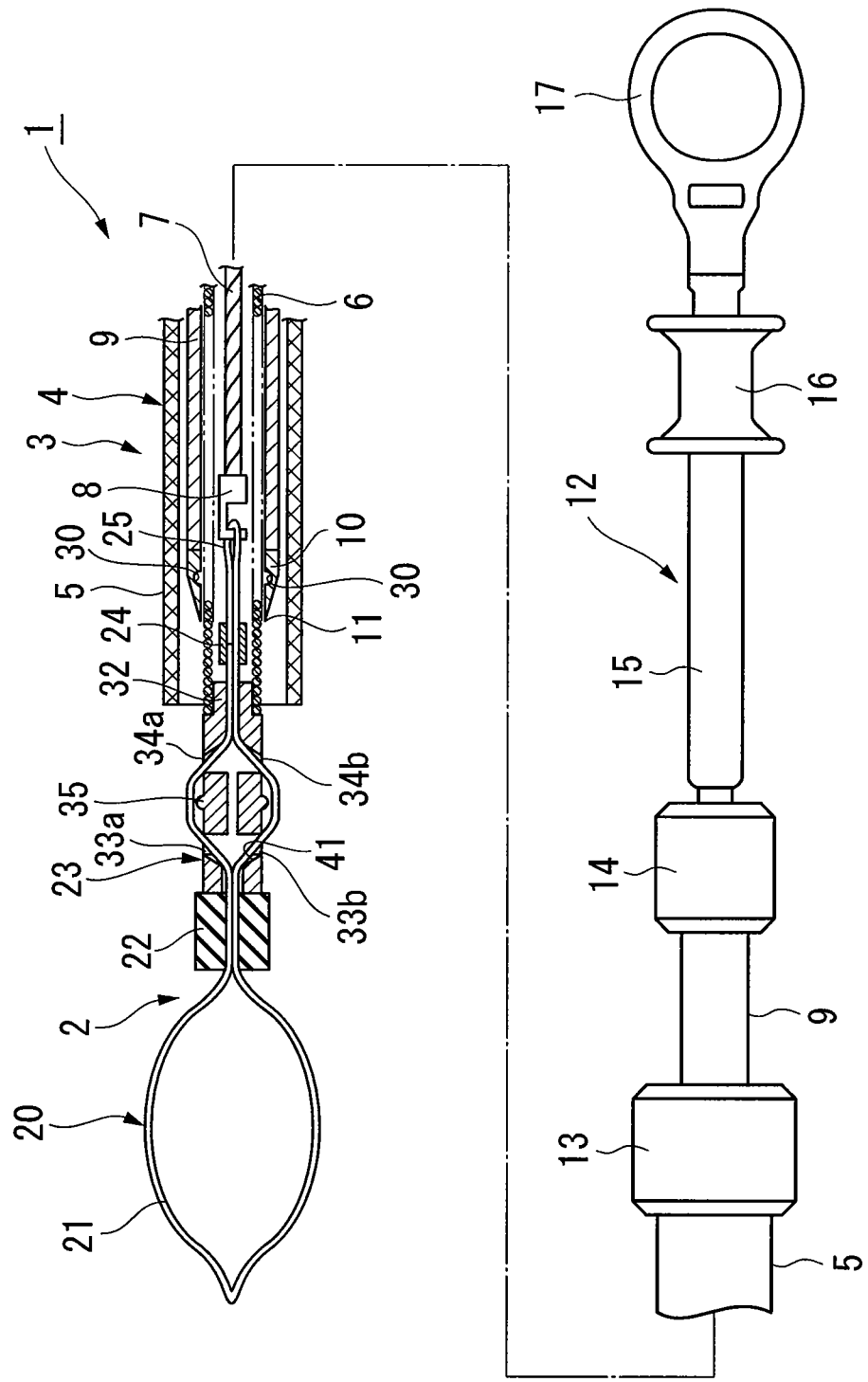
FIG. 1 is a diagram illustrating a configuration of a medical ligature instrument according to an embodiment of the present invention.

Hereinafter, a first embodiment of the present invention will be described with reference to FIGS. 1 to 7. As shown in FIG. 1, a medical suture and ligature instrument 1 includes a medical ligature tool (medical suture and ligature tool) 2 which is detained in a body and an operation unit 3 which allows the medical ligature tool 2 to be detachably attached to the distal end thereof. The operation unit 3 has an elongated insertion portion 4 of which the distal end is inserted into a channel of an endoscope (not illustrated) and of which the proximal end is drawn out via the endoscope to the outside thereof. The insertion portion 4 includes a flexible outer sheath 5 and an inner sheath 6 is inserted into the outer sheath 5 so as to extend and retract along the axial direction thereof. A flexible operating wire 7 is inserted through the inner sheath 6 so as to extend and retract along the axial direction. An engaging member 8 having a hook shape is fixed to the distal end of the operating wire 7. A flexible cutting sheath 9 is fitted onto the outer periphery of the inner sheath 6 so as to extend and retract along the axial direction. A cutting member 10 as means for cutting a ligature wire to be described later is fixed to the distal end of the cutting sheath 9. The cutting member 10 has an annular shape covering the outer periphery of the inner sheath 6 and a cutting edge 11 forming an acute angle about the axial direction are formed around the distal end thereof. A concave portion 30 as a cutting-side engaging portion is disposed in the inner periphery of the cutting member 10. A plurality of (for example, two or three) concave portions 30 is formed in the peripheral direction of the cutting member 10 and is formed as a recessed portion having substantially a semi-circular shape. The cutting member 10 is made of a metal material such as stainless steel.

Here, the outer sheath 5 is made of flexible plastic such as polyethylene and PTFE (polytetrafluoroethylene) and has an inner diameter of $\phi$2 to $\phi$5 mm. The inner sheath 6 and the cutting sheath 9 are also made of flexible plastic such as polyethylene and PTFE, but may additionally include a metal mesh added thereto or may be made of a metal coil. The operating wire 7 is made of a twisted metal wire of stainless steel or the like.

The distal end of the insertion portion 4 having the above-mentioned configuration is provided with a handle operating section 12 for allowing an operator to perform an operation thereof outside the body. The handle operating section 12 includes a handle 13 to which the proximal end of the outer sheath 5 is fixed, a cutting operating portion 14 to which the proximal end of the cutting sheath 9 is fixed, an elongated operating section body 15 to which the proximal end of the inner sheath 6 is fixed, and a slider 16 which is attached to the operating section body 15 so as to extend and retract along the longitudinal direction. The proximal end of the operating wire 7 is fixed to the slider 16. A finger laying ring 17 is disposed at the proximal end of the operating section body 15.

The medical ligature tool 2 fitted to the distal end of the operation unit 3 includes a ligature wire 20 serving as a suture and ligature member for ligaturing a biological tissue. The ligature wire 20 is a thread made of a synthetic resin such as nylon (polyamide resin) and polyolefin, a fine metal wire of stainless steel or the like, silk, a bioabsorbable material and has a diameter of $\phi$0.2 to $\phi$1 mm. The ligature wire forms a loop portion 21 by folding back the wire at the center thereof in the longitudinal direction. As the ligature wire 20, a single wire can be used, but a twisted wire or a woven wire may also be used. End portions of the ligature wire 20 which form a pair by forming the loop portion 21 are press-fitted so that it penetrates a hole of a tube-shaped stopper 22. The stopper 22 is a fixing member for allowing the ligature wire 20 to extend and retract. When the stopper 22 is extended toward the distal end with the ligature wire 20 bound, the diameter of the loop portion 21 is reduced. When the stopper is retracted, the diameter of the loop portion 21 is enlarged. The stopper 22 is made of rubber such as silicon rubber and fluorine rubber or various thermoplastic elastomers and a knot of a thread may be used instead of the tube-shaped member. A pair of end portions of the ligature wire 20 drawn out of the stopper 22 is inserted through a tube-shaped holding member 23, and one end thereof is folded back and inserted into a connecting pipe 24 as a fixing tool into which the other end of the ligature wire 20 is inserted, where both end portions are fixed with an adhesive or the like. A folding-back portion 25 on the proximal side of the ligature wire 20 is formed in a loop shape, which engages with an engaging member 8 of the operating wire 7.

Figure 2:
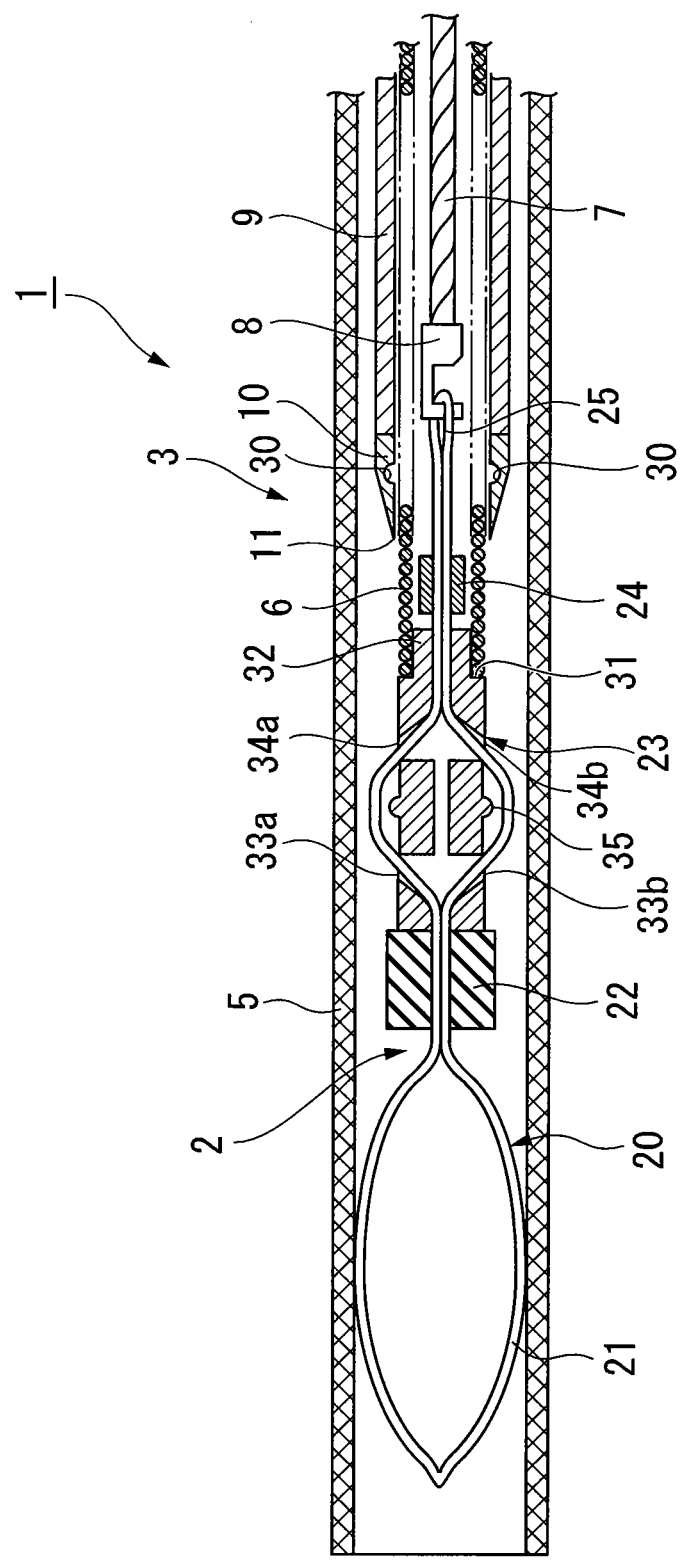
FIG. 2 is an enlarged diagram illustrating a holding member and a cutting member.

As shown in the enlarged diagram of FIG. 2, in the holding member 23, the proximal end is reduced in diameter by a stepped portion 31 and the outer diameter of the proximal diameter-reduced portion 32 formed by the stepped portion 31 has a size sufficient to be inserted into the inner sheath 6. In the holding member 23, distal lateral holes 33a and 33b and proximal lateral holes 34a and 34b penetrating the inner periphery and the outer periphery of the holding member 23 are disposed in the longitudinal direction between the distal end surface and the stepped portion 31; and a holding portion for holding the ligature wire 20 is formed between the distal lateral holes 33a, 33b and the proximal lateral holes 34a, 34b. A pair of distal lateral holes 33a and 33b is disposed in the diameter direction of the holding member 23, is inclined from the distal and inner peripheral side to the proximal and outer peripheral side, and is formed with a hole diameter through which the ligature wire 20 can be inserted. Similarly, a pair of proximal lateral holes 34a and 34b is disposed in the diameter direction of the holding member 23, is inclined from the distal and outer peripheral side to the proximal and inner peripheral side, and is formed with a hole diameter through which the ligature wire 20 can be inserted. Protrusions 35 as a holding-side engaging portion are disposed to protrude between the distal lateral hole 33a and the proximal lateral hole 33b which are adjacent to each other in the longitudinal direction of the holding member 23.

The protrusions 35 have a shape which can engage the concave portion 30 of the cutting member 10 and are disposed at positions corresponding to the number of concave portions 30. The holding member 23 is made of a metal material such as stainless steel or plastic such as polypropylene, ABS (acrylonitrile-butadiene resin), and polycarbonate.

Next, operations of this embodiment will be described.

Figure 3:
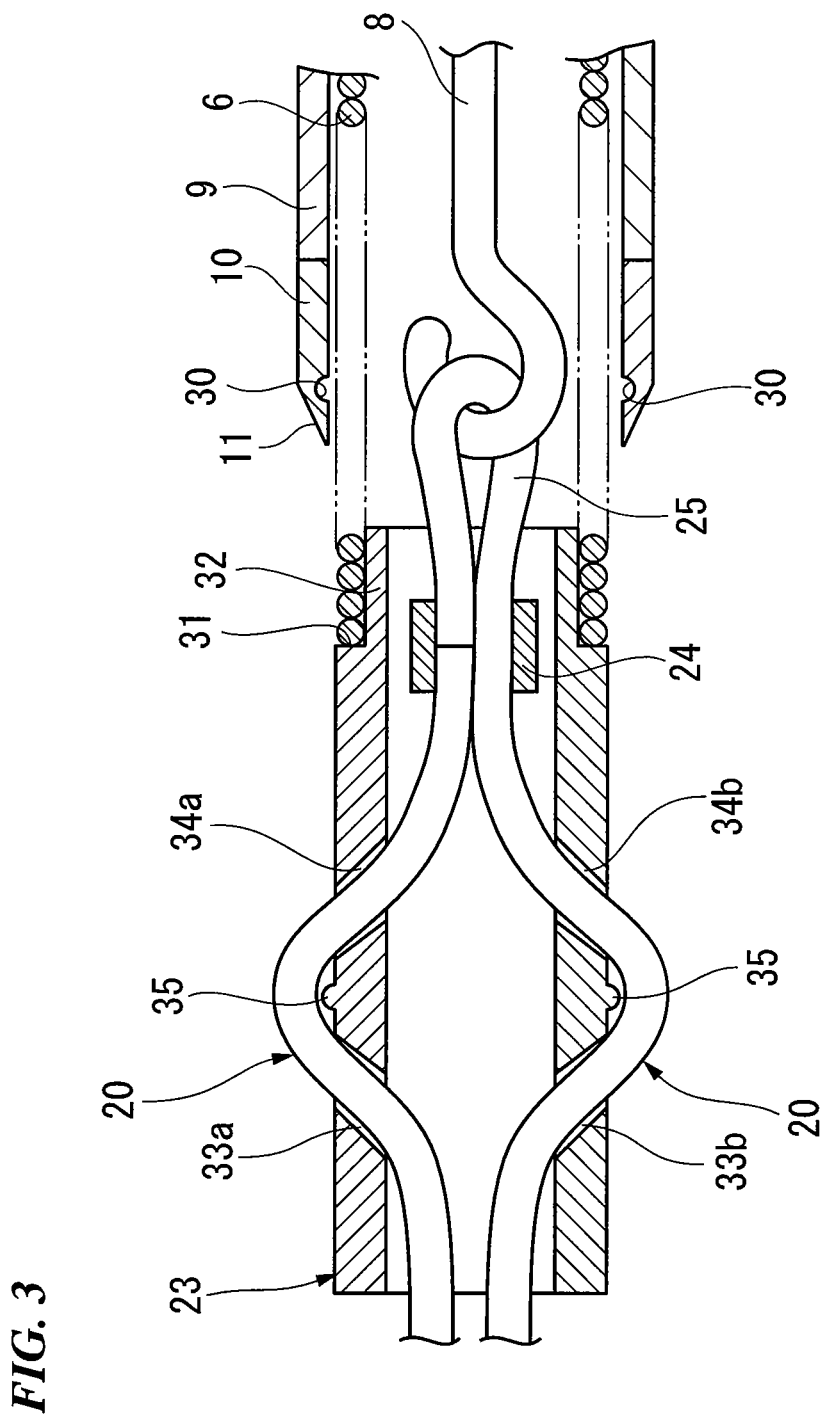
FIG. 3 is a diagram illustrating a state where a medical ligature tool is fitted to an operation unit and is received in an outer sheath.

First, the medical ligature tool 2 is mounted on the operation unit 3. Specifically, the operating wire 7 is extended by operating the slider 16 and the engaging member 8 on the distal end of the operating wire 7 is protruded from the distal openings of the outer sheath 5 and the inner sheath 6. In this state, when the folding-back portion 25 of the ligature wire 20 is hooked and locked to the engaging member 8, the operating wire 7 is retreated by drawing back the slider 16. Accordingly, the engaging member 8 is drawn into the inner sheath 6 and the proximal diameter-reduced portion 32 of the holding member 23 is inserted into and supported by the inner sheath 6. Thereafter, the outer sheath 5 is made to advance by operating the handle 13. Accordingly, as shown in FIG. 3, the ligature wire 20 is received in the outer sheath 5 and the loop portion 21 contracts.

Figure 4:
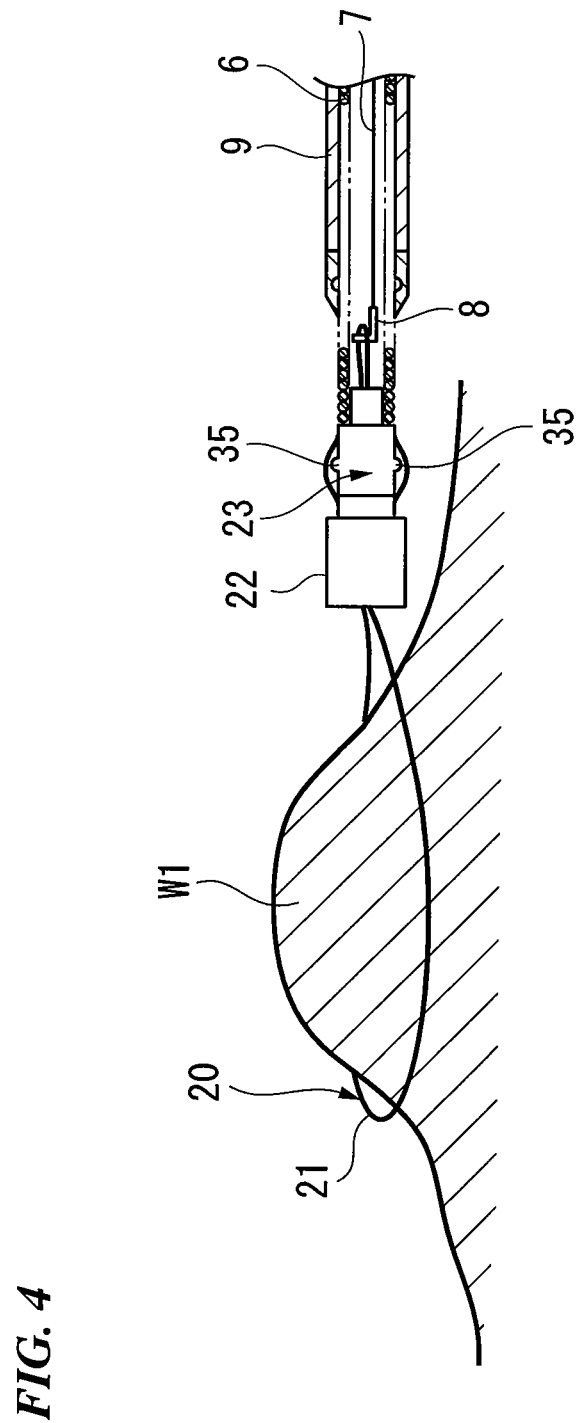
FIG. 4 is a diagram illustrating a procedure of ligaturing a pathological lesion portion, which shows a state where a ligature wire is hooked to the pathological lesion portion.
Figure 5:
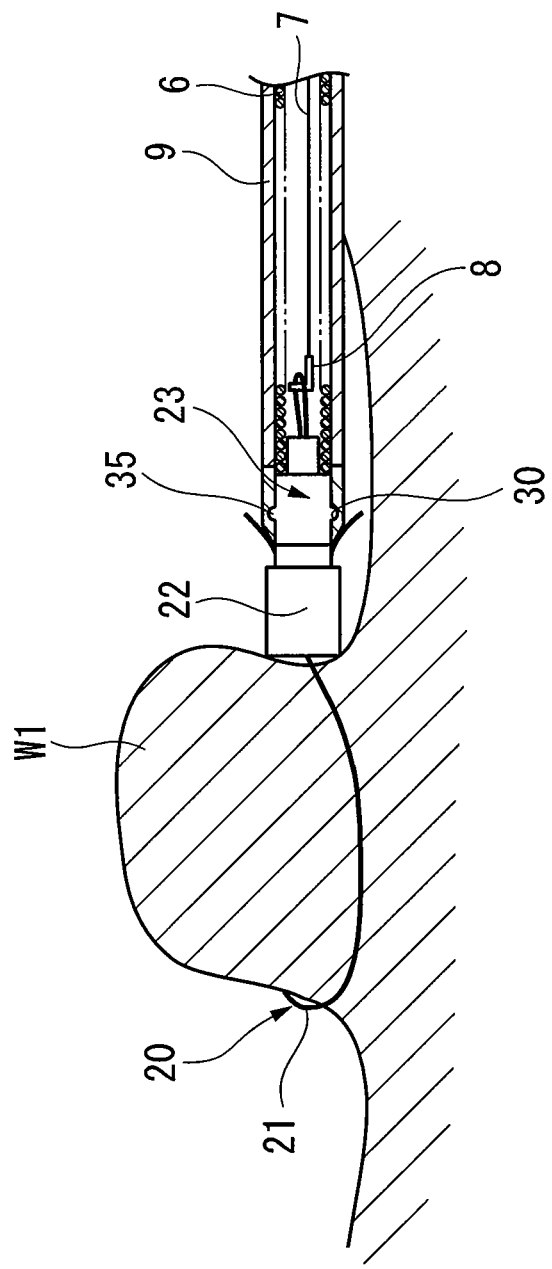
FIG. 5 is a diagram illustrating a procedure of ligaturing a pathological lesion portion, which shows a state where a ligature wire is cut after biological tissue is bound tight.

When the medical ligature tool 2 is mounted, the insertion portion 4 of the operation unit 3 is inserted through the channel of the endoscope and is inserted into the body along with the endoscope. When the distal end of the insertion portion 4 is guided to a target site in the body, the outer sheath 5 is retreated by operating the handle 13 while observing a pathological lesion portion such as polyps with the endoscope. As shown in FIG. 1, the loop portion 21 of the ligature wire 20 protrudes from the distal opening of the outer sheath 5 and is restored by the elasticity thereof to enlarge the diameter. Next, as shown in FIG. 4, the loop portion 21 of the ligature wire 20 is hooked to a root of a pathological lesion portion W1 while observing the pathological portion with the endoscope. In this state, when the operating wire 7 is retreated by operating the slider 16, the proximal end of the ligature wire 20 is drawn into the inner sheath 6 via the engaging portion 8 as shown in FIG. 5. Accordingly, the stopper 22 and the holding member 23 are relatively moved toward the distal end of the ligature wire 20.

As a result, the diameter of the loop portion 21 of the ligature wire 20 is reduced to tightly bind the pathological lesion portion W1. In this way, the pathological lesion portion is ligatured with the ligature wire 20, thereby stopping the flow of blood to the pathological lesion portion W1.

When the cutting sheath 9 is extended by operating the cutting operating section 14 with the slider 16 kept in place, the cutting sheath 9 is guided by the inner sheath 6 so as to extend. Accordingly, the cutting member 10 disposed on the distal end of the cutting sheath 9 extends so as to cover the outer periphery of the holding member 23 and the cutting edge 11 rubs and cuts the ligature wire 20 held by the holding portion in the path thereof, that is, the ligature wire 20 exposed from the proximal lateral holes 34a and 34b. At this time, since the proximal end portion of the ligature wire 20 is suspended by the operating wire 7 and a tension is applied thereto, the ligature wire can be easily cut by the cutting edge 11. The ligature wires 20 passing through the proximal lateral holes 34a and 34b are not cut simultaneously, but may be cut individually. However, since the ligature wires 20 are coupled to the connecting pipe 24, the tension is maintained even when only one end is cut. Accordingly, the cutting effect by the cutting edge 11 is not varied.

Figure 6:
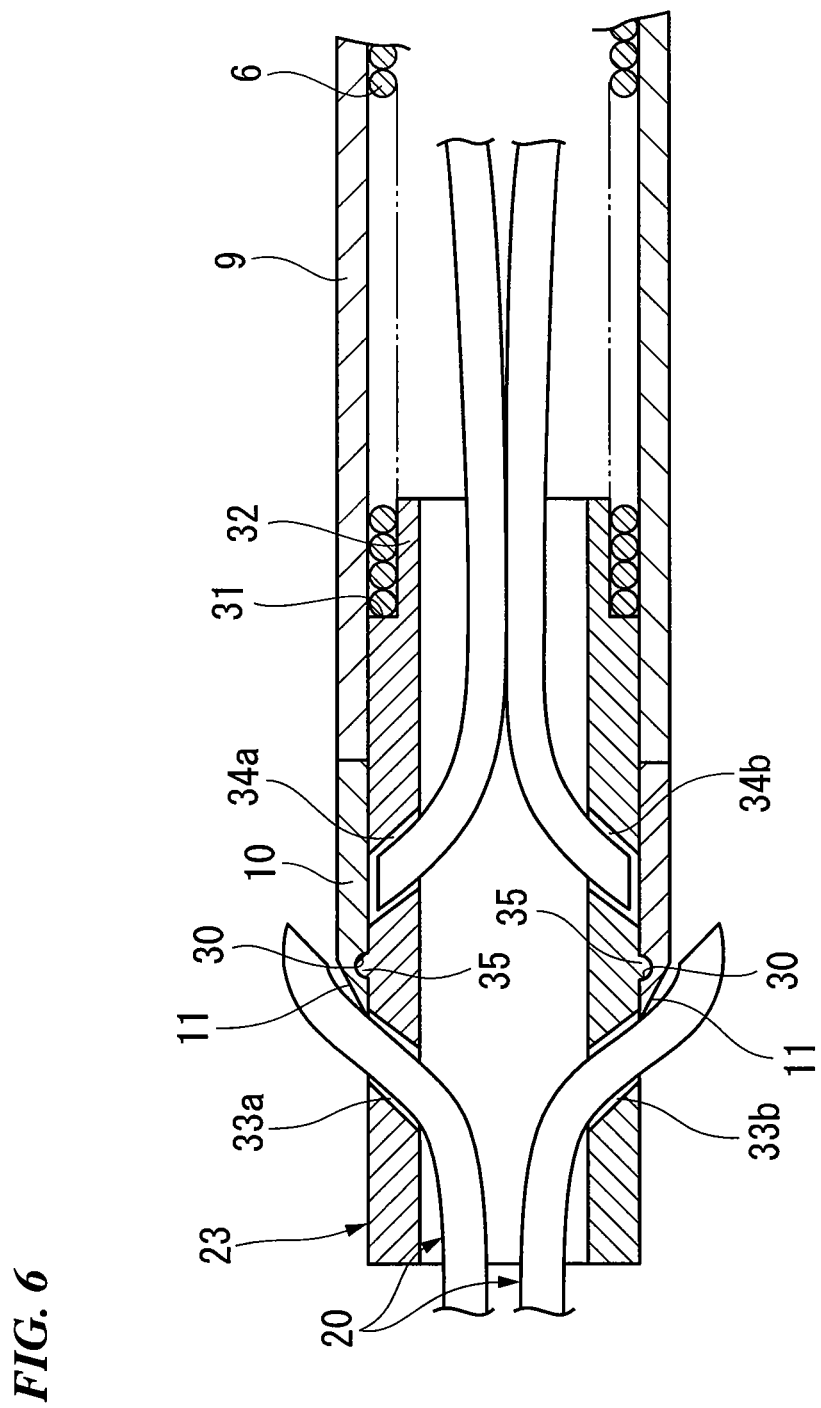
FIG. 6 is a cross-sectional view illustrating a state where the holding member engages with the cutting member.

Here, as shown in FIG. 6, when the concave portions 30 and the protrusions 35 engage each other, the cutting member 10 is stopped. Since the distance from the distal end of the cutting edge 11 to the concave portions 30 is shorter than the distance from the protrusions 35 to the proximal peripheral edge of the distal lateral holes 33a and 33b, the cutting edge 11 does not cut the ligature wire 20 passing through the distal lateral holes 33a and 33b. By cutting off the ligature wire 20 passing over the outer periphery of the holding member 23, the portion of the medical ligature tool 2 detained in the body is separated from the operation unit 3. Accordingly, when the cutting sheath 9 is retracted by operating the cutting operating section 14 and then the insertion portion 4 of the operation unit 3 is pulled out of the channel of the endoscope, the cut end of the ligature wire 20 is detached from the distal lateral holes 33a and 33b and the loop portion 21 is detained in the body. On the other hand, since the holding member 23 engages with the cutting member 10, the holding member 23 is pulled out of the body along with the operation body 3 without being left in the body.

According to this embodiment, the protrusions 35 are disposed between the lateral holes 33a, 33b, 34a, and 34b of the holding member 23 and the concave portions 30 engaging with the protrusions 35 are disposed in the cutting member 10. Accordingly, it is possible to allow the cutting member 10 to engage with the holding member 23 after the cutting member cuts the ligature wire 20 in the proximal lateral holes 34a and 34b. Therefore, it is possible to leave the holding member 23 fitted to the operation unit 3 even after the ligature wire 20 is cut. Accordingly, it is possible to draw out the holding member 23 along with the operation unit 3 from the body. Consequently, there is no need to insert other treatment instruments in order to separate the holding member 23 from the ligature wire 20, and it is possible to facilitate surgical procedure and to reduce operation time. Since the operation of cutting the ligature wire 20 and the operation of engaging the holding member 23 can be continuously carried out only by allowing the cutting sheath 9 to advance, surgical procedure is facilitated.

Figure 7:
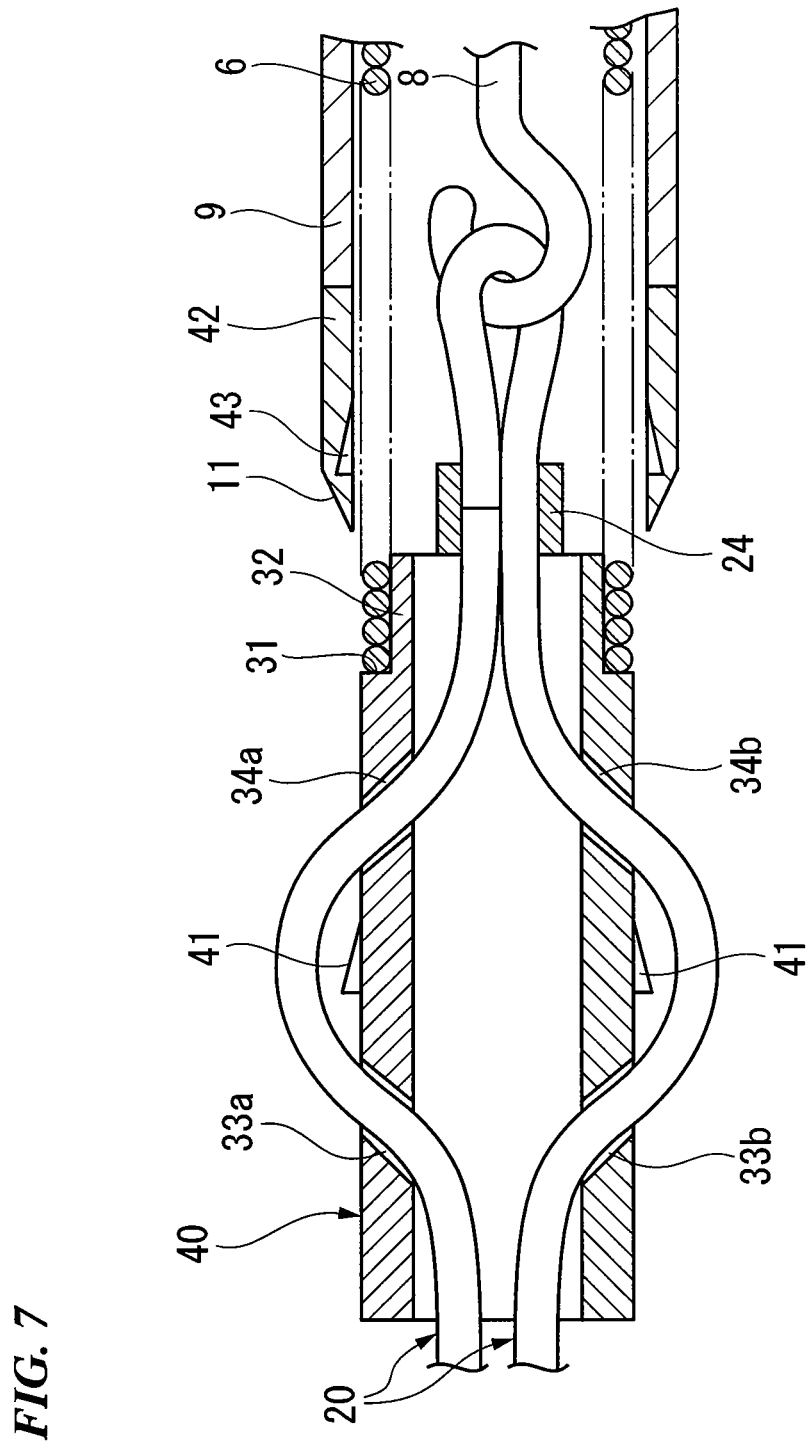
FIG. 7 is an enlarged diagram illustrating a holding member and a cutting member.
Figure 8:
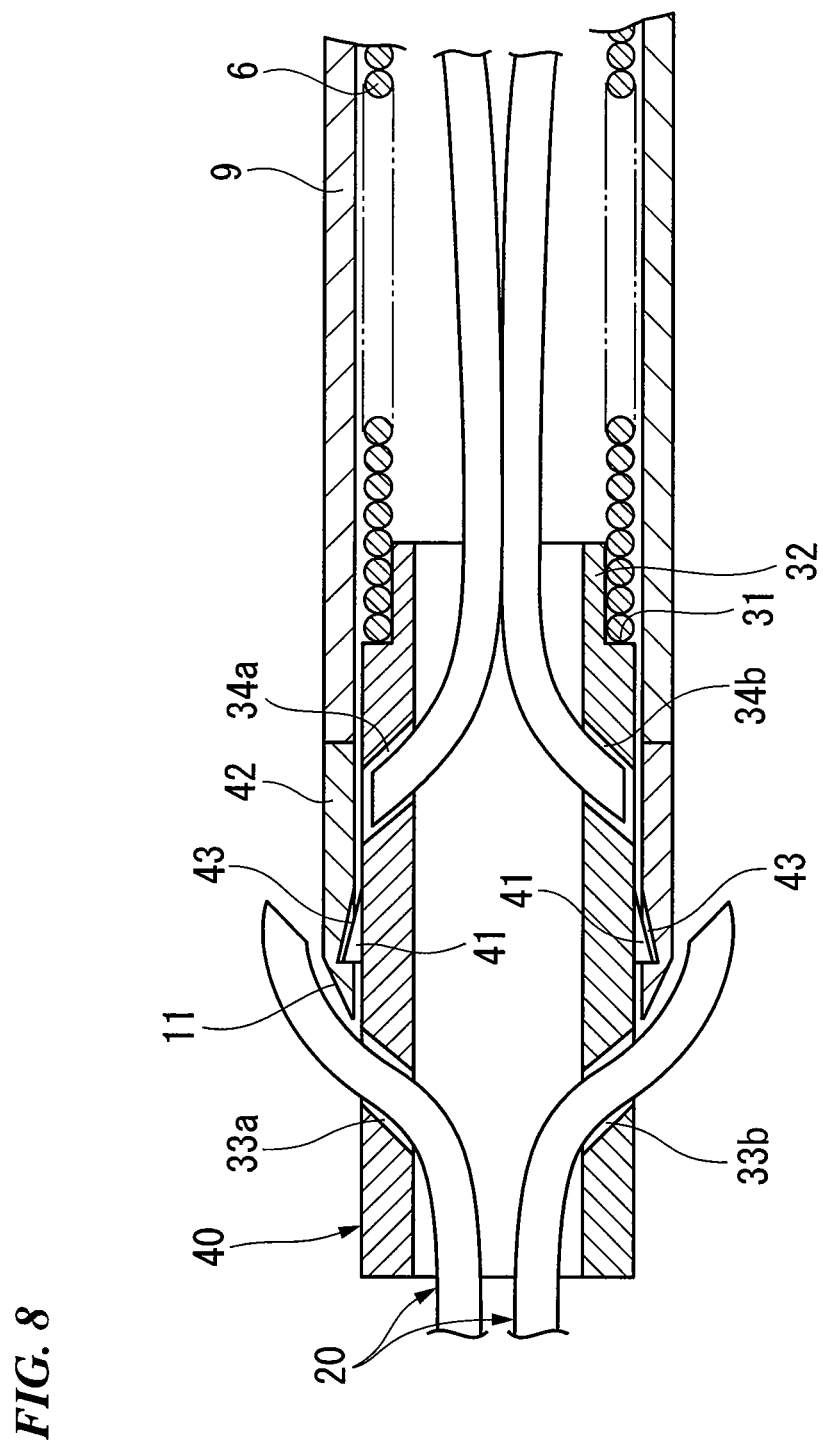
FIG. 8 is a cross-sectional view illustrating a state where the holding member engages the cutting member.

Like the holding member 40 shown in FIG. 7, a protrusion 41 having a triangular wedge shape in a side view may be provided as the holding-side engaging portion. In the cutting member 42, a concave portion 43 engaging with the protrusion 41 and having a triangular shape in a side view may be provided as the cutting-side engaging portion. The number and arrangement of the protrusions 41 and the concave portions 43 are equal to those of the protrusions 35 and the concave portions 30 shown in FIG. 2. As shown in FIG. 8, the protrusions 41 and the concave portions 43 engage with each other after cutting the ligature wire 20. However, since the proximal side of each protrusion 41 has a slow slope, it facilitates the concave portions 43 to engage with the cutting member 42.

In addition, since the distal side of each protrusion 41 has a plane perpendicular to the axial direction, the cutting member 42 is not separated easily from the protrusions 41 after they engage each other. Accordingly, it is possible to reliably prevent the separation of the holding member 40.

Second Embodiment

Figure 9:
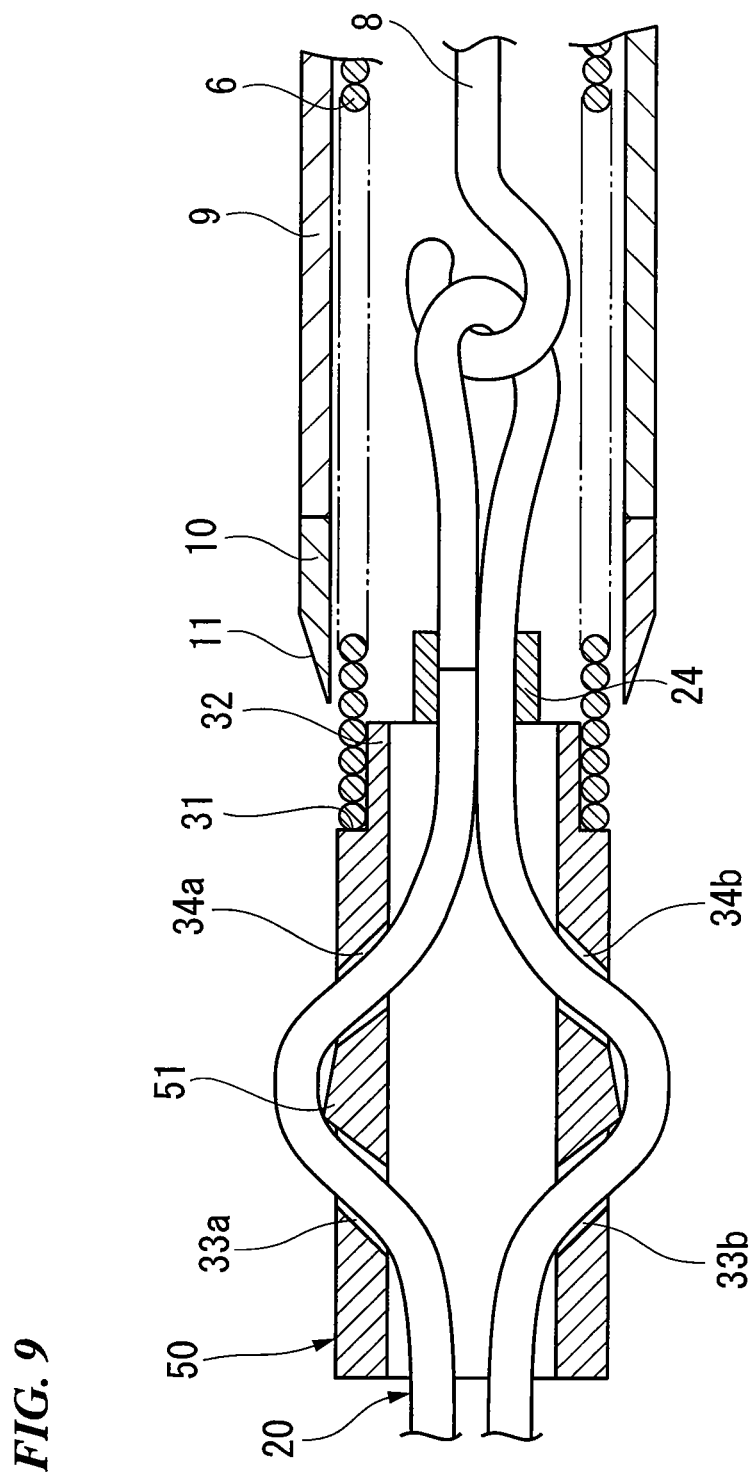
FIG. 9 is an enlarged diagram illustrating a holding member and a cutting member.
Figure 10:
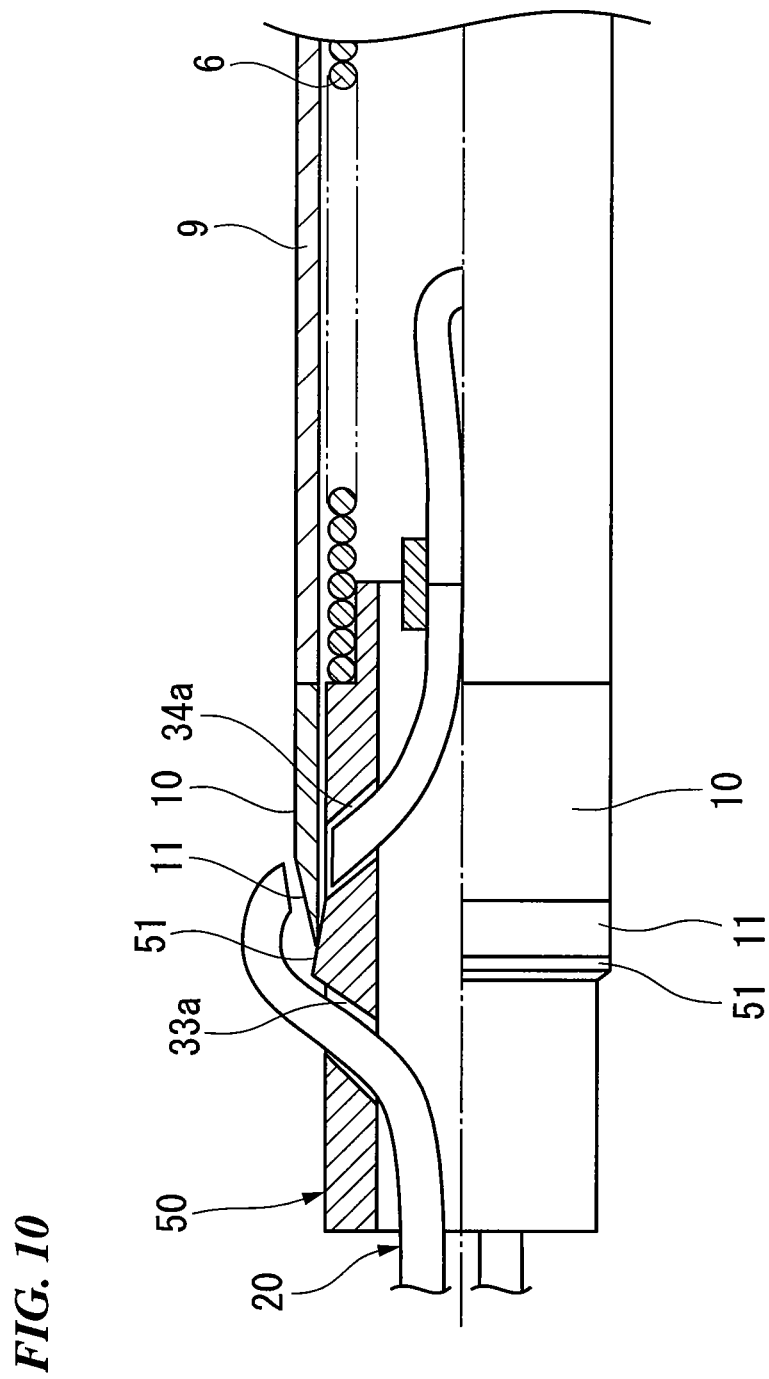
FIG. 10 is a cross-sectional view illustrating a state where the holding member engages the cutting member.

A second embodiment of the present invention will be described with reference to FIGS. 9 and 10. The same elements as the first embodiment are denoted by the same reference numerals and repeated descriptions are omitted.

A medical suture and ligature instrument according to this embodiment is different from the first embodiment in the configurations of the holding member and the cutting member. As shown in FIG. 9, a holding member 50 has an annular tapered portion 51 as the holding-side engaging portion disposed between the distal lateral holes 33a and 33b and the proximal lateral holes 34a and 34b. In a side sectional view, the tapered portion 51 extends outward in the diameter direction and toward the proximal end from the distal lateral holes 33a, is bent at an angle of more than and equal to 90 degrees, and reaches the position of the proximal lateral hole 34a while forming a slow slope. On the other hand, the cutting member 10 has a cutting edge 11 disposed at the distal end of the annular portion. The cutting member 10 is formed of a metal material, but can change its shape due to the slight elasticity.

Operations of this embodiment will be described.

When a pathological lesion portion W1 is ligatured with the ligature wire 20, the cutting member 10 is extended, and the exposed portion of the ligature wire 20 is rubbed and cut with the cutting edge 11. At this time, as shown in FIG. 10, the cutting edge 11 advances to the distal end over the proximal lateral hole 34a, the cutting edge 11 is slightly deformed to introduce the slope of the tapered portion 51 inside. As a result, the slope of the tapered portion 51 is press-fitted substantially against the inner peripheral surface of the cutting edge 11. Accordingly, the ligature wire 20 ligaturing the pathological lesion portion W1 is detained in the body and the holding member 50 maintains the state where it is fitted to the operation unit 3. Therefore, when the operation unit 3 is pulled out, the holding member 50 is removed from the body.

In this embodiment, since the tapered portion 51 is used as the holding-side engaging portion and the inner peripheral surface of the cutting member 10 is used as the cutting-side engaging portion engaging therewith, it is not necessary to provide the concave portion on the cutting member 10. Accordingly, it is possible to facilitate the manufacturing and to reduce the manufacturing cost. Since the holding member 50 and the cutting member 10 do not require high dimensional precision, the manufacturing or assembly will become easier. Other advantages are equal to those of the first embodiment.

In this embodiment, the cutting edge 11 forms an acute edge by inclining the cutting edge so that the outer diameter increases from the distal edge to the proximal edge, but may form an acute edge by inclining the cutting edge from the outer periphery of the distal end to the inner periphery of the proximal end. The cutting edge 11 having the above-mentioned shape can easily engage the tapered portion 51 of the holding member 50.

Third Embodiment

A third embodiment of the present invention will be described with reference to FIG. 11. The same elements as the first embodiment are denoted by the same reference numerals and repeated descriptions are omitted.

A medical suture and ligature tool according to this embodiment is different from the first embodiment in the configurations of the holding member and the cutting member. As shown in FIG. 11, a holding member 60 has a protrusion 61 as the holding-side engaging portion disposed at a position displaced by about 90 degrees in the peripheral direction from the position of the proximal lateral hole 34a. A protrusion 61 protrudes outward in the diameter direction and two protrusions are disposed in the diameter direction of the holding member 60. Each protrusion 61 has substantially a cylindrical shape. Other configurations of the holding member 60 are equal to those of the first embodiment.

In a cutting member 62, the cutting edge 11 is divided into two portions by notching two positions in the peripheral direction, thereby forming arc-shaped cutting edges 11a and 11b. The notched portions serve as guide portions 63 for receiving the protrusions 61. The guide portions 63 are formed with a gap of 180° in the peripheral direction to correspond to the positions of the protrusions 61. Concave portions 64 as the cutting-side engaging portion are disposed at positions closer to the proximal end than the guide portions 63 in the longitudinal direction of the cutting member 62 and on the inner periphery of the cutting member 62. The concave portions 64 have a shape engaging with the protrusions 61.

Next, operations of this embodiment will be described.

When a pathological lesion portion W1 is ligatured with the ligature wire 20, the cutting member 62 is extended. At this time, since the guide portions 63 are disposed to correspond to the positions of the protrusions 61, the cutting edges 11a and 11b cut the ligature wire 20 without coming in contact with the protrusions 61. In the meantime, the protrusions 61 enter the guide portions 63, the cutting member 62 completely cuts the portion of the ligature wire 20 exposed from the proximal lateral holes 34a and 34b, and then the protrusions 61 engage with the concave portions 64 of the cutting member 62. Accordingly, the ligature wire 20 ligaturing the pathological lesion portion W1 is detained in the body and the holding member 60 maintains a state where it is fitted to the operation unit 3 sides. Therefore, when the operation unit 3 is pulled out, the holding member 60 is recovered from the body together.

In this embodiment, the guide portions 63 are disposed in the cutting edges 11a and 11b to correspond to the positions of the protrusions 61 of the holding member 60. Accordingly, at the time of cutting the ligature wire 20 with the cutting member 62, it is possible to prevent the cutting edges 11a and 11b from interfering with the protrusions 61 and to smoothly cut the ligature wire 20. Since the concave portions 64 are positioned closer to the proximal end than the cutting edges 11a and 11b, it is possible to allow the holding member 60 to engage with the cutting member 62 after completely cutting the ligature wire 20.

Figure 11:
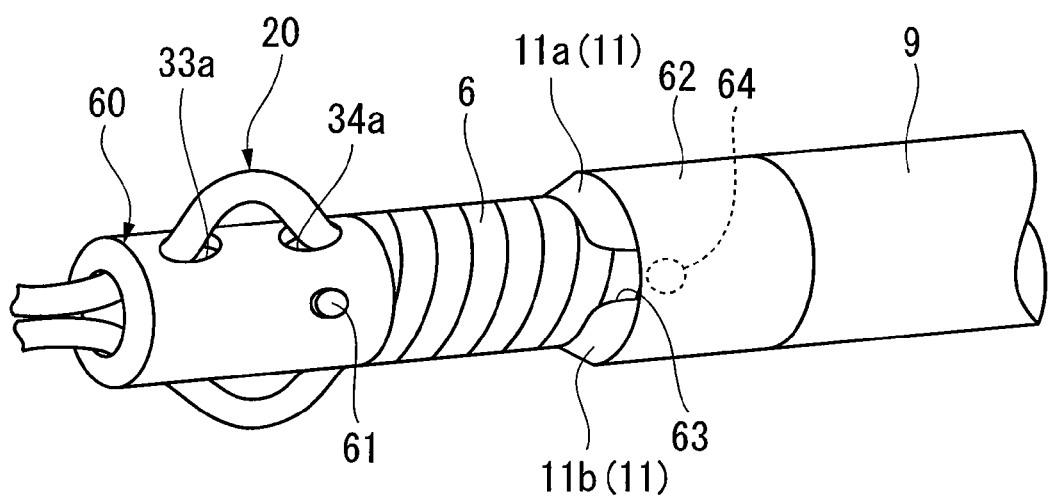
FIG. 11 is a perspective view of a holding member and a cutting member.

The positions of the protrusions 61 and the positions of the concave portions 64 are not limited to the positions shown in FIG. 11, but may be any position so long as they can engage with each other after cutting the ligature wire 20. In addition, by disposing a rotation stopper for preventing the rotation about the axis of the inner sheath 6 on the distal side of the insertion portion or in the handle operating section 12 (see FIG. 1), it is possible to reliably perform the cutting of the ligature wire 20 and the engagement of the holding member 60. When the holding member 60 is positioned and fitted to the inner sheath 6 and the rotation thereof is prevented, it is possible to reliably perform the cutting of the ligature wire 20 and the engagement of the holding member 60. In an example of such a configuration, a concave portion or a convex portion is formed in the longitudinal direction in the proximal diameter-reduced portion 32 (see FIG. 2) of the holding member 60 and a convex portion or a concave portion engaging therewith is formed on the inner peripheral surface on the distal side of the inner sheath 6. The convex portion or the concave portion is disposed so that the protrusion 61 of the holding member 60 and the concave portion 64 of the cutting member 62 correspond to each other in the peripheral direction.

Fourth Embodiment

Figure 12:
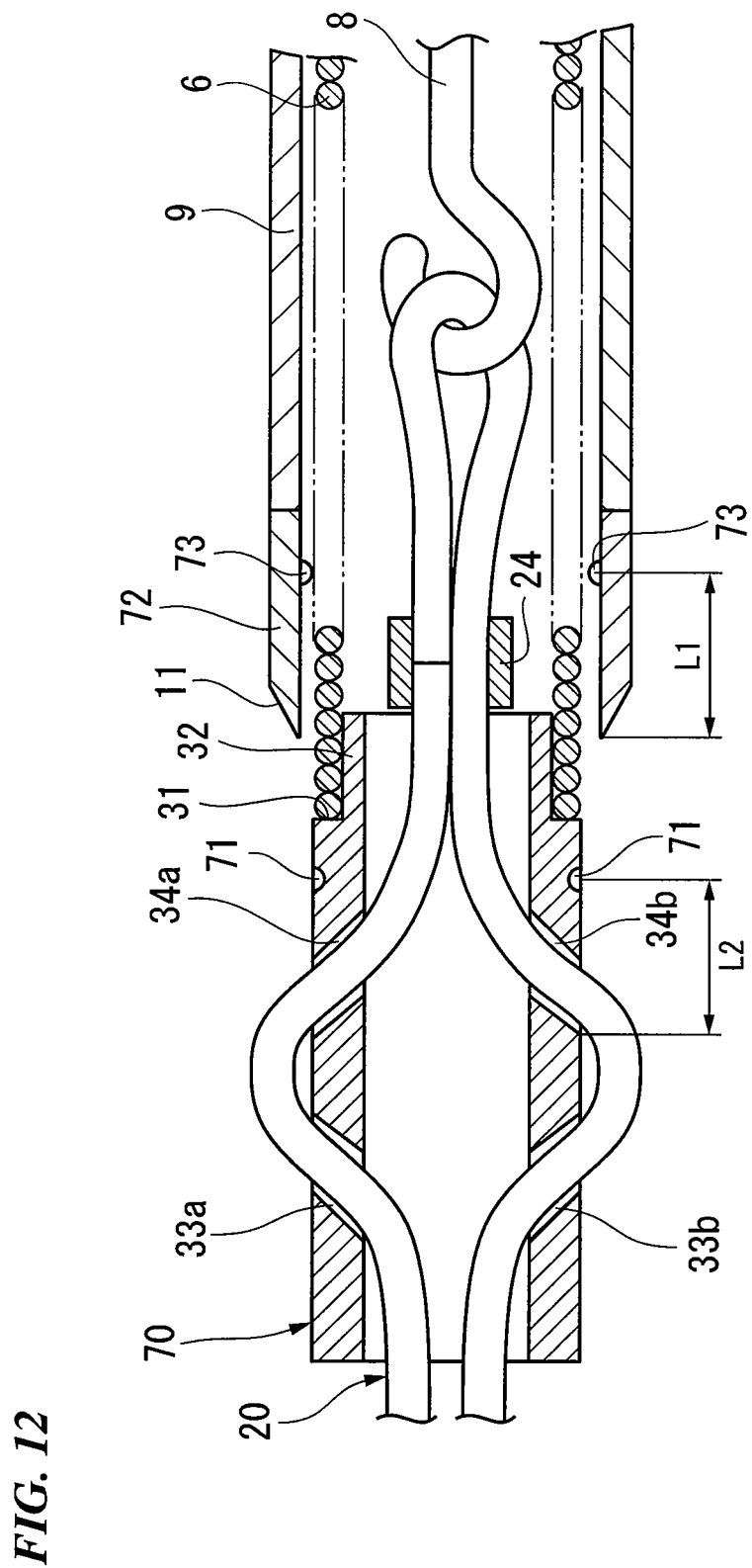
FIG. 12 is an enlarged diagram illustrating a holding member and a cutting member.
Figure 13:
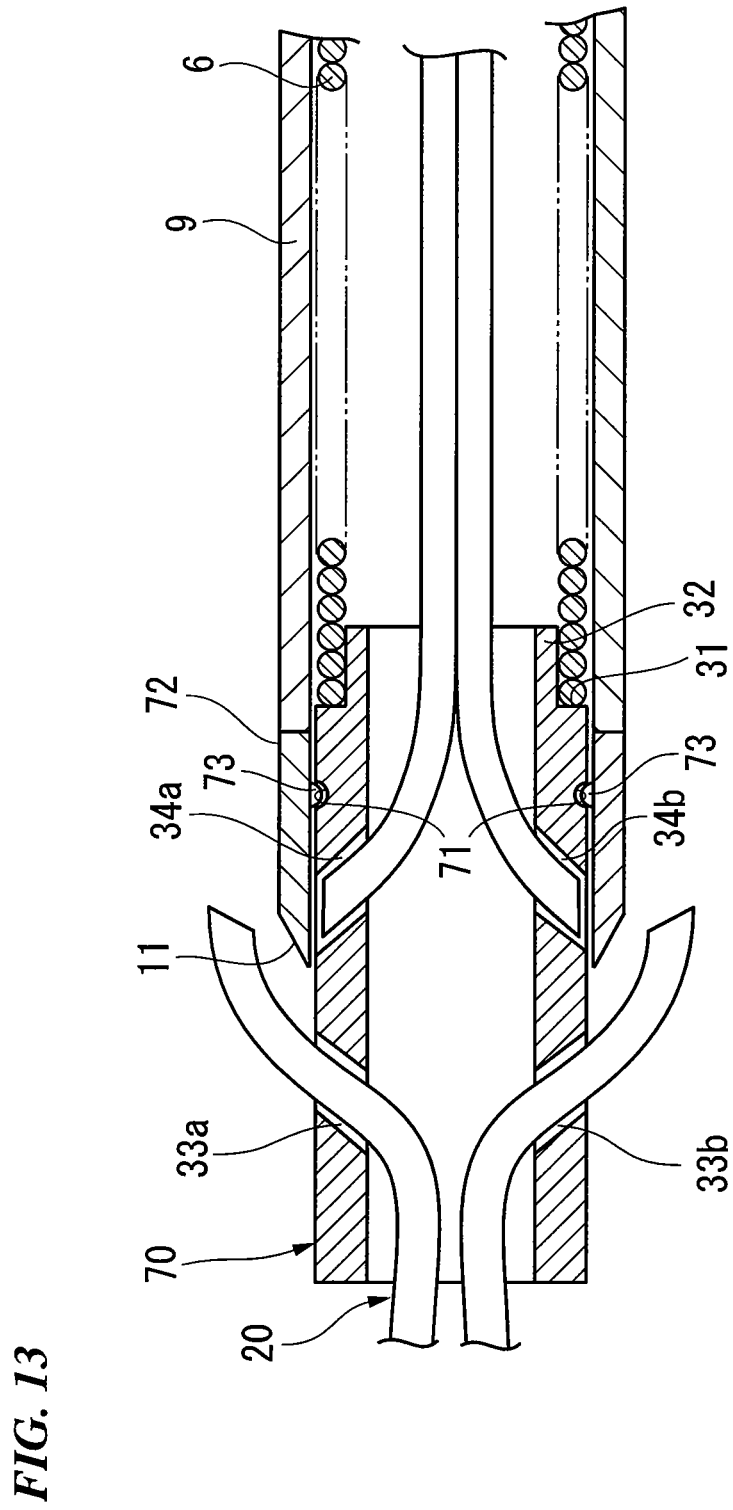
FIG. 13 is a cross-sectional view illustrating a state where the holding member engages the cutting member.

A fourth embodiment of the present invention will be described with reference to FIGS. 12 to 14. The same elements as the first embodiment are denoted by the same reference numerals and repeated descriptions are omitted.

A medical suture and ligature instrument according to this embodiment is different from the first embodiment in the configuration of the holding member and the configuration of the cutting member. As shown in FIG. 12, a holding member 70 has a concave portion 71 as the holding-side engaging portion formed between the proximal lateral holes 34a, 34b and the proximal diameter-reduced portion 32. Although two concave portions 71 are disposed to correspond to the positions of the proximal lateral holes 34a and 34b in the peripheral direction, the positions in the peripheral direction and the number of the concave portions 71 are not limited to them.

The cutting member 72 has protrusions 73 as the cutting-side engaging portion formed in the inner periphery closer to the proximal end than the cutting edge 11. The protrusions 73 have a shape engaging with the concave portions 71 of the holding member and correspond to the concave portions 71 in position in the peripheral direction. Here, a distance L1 in the longitudinal direction from the distal end of the cutting edge 11 to the positions of the protrusions 73 is larger than a distance L2 from the proximal edge of the proximal lateral hole 34b of the holding member 70 to the concave portions 71.

Next, operations of this embodiment will be described.

When a pathological lesion portion W1 is ligatured with the ligature wire 20, the cutting member 72 is extended. At this time, when the ligature wire 20 exposed from the proximal lateral holes 34a and 34b are cut off with the cutting edge 11 and then the cutting member 72 further extends, as shown in FIG. 13, the protrusions 73 are inserted into the concave portions 71, and the cutting member 72 is no longer extended and retracted, whereby the holding member 70 engages the cutting member 72. Accordingly, the ligature wire 20 ligaturing the pathological lesion portion W1 is detained in the body and the holding member 70 is recovered out of the body along with the operation unit 3.

In this embodiment, since the concave portions 71 are used as the holding-side engaging portion, the holding-side engaging portion does not interfere with the cutting edge 11 and thus the ligature wire 20 can be smoothly cut. Since the distance L1 from the cutting edge 11 to the protrusions 73 of the cutting member 72 is made to be longer than the distance L2 from the distal edge of the proximal lateral holes 34a and 34b of the holding member 70 to the concave portions 71, it is possible to allow the holding member 70 to engage with the cutting member 72 after completely cutting the ligature wire 20. Here, when the distance L1 from the distal end of the cutting edge 11 to the protrusions 73 is made to be shorter than the distance L2 from the distal edge of the proximal lateral holes 34a and 34b, it is possible to reduce the time lag until the holding member engages after the ligature wire 20 is cut and to completely prevent the separation of the holding member 70 and the like.

Figure 14:
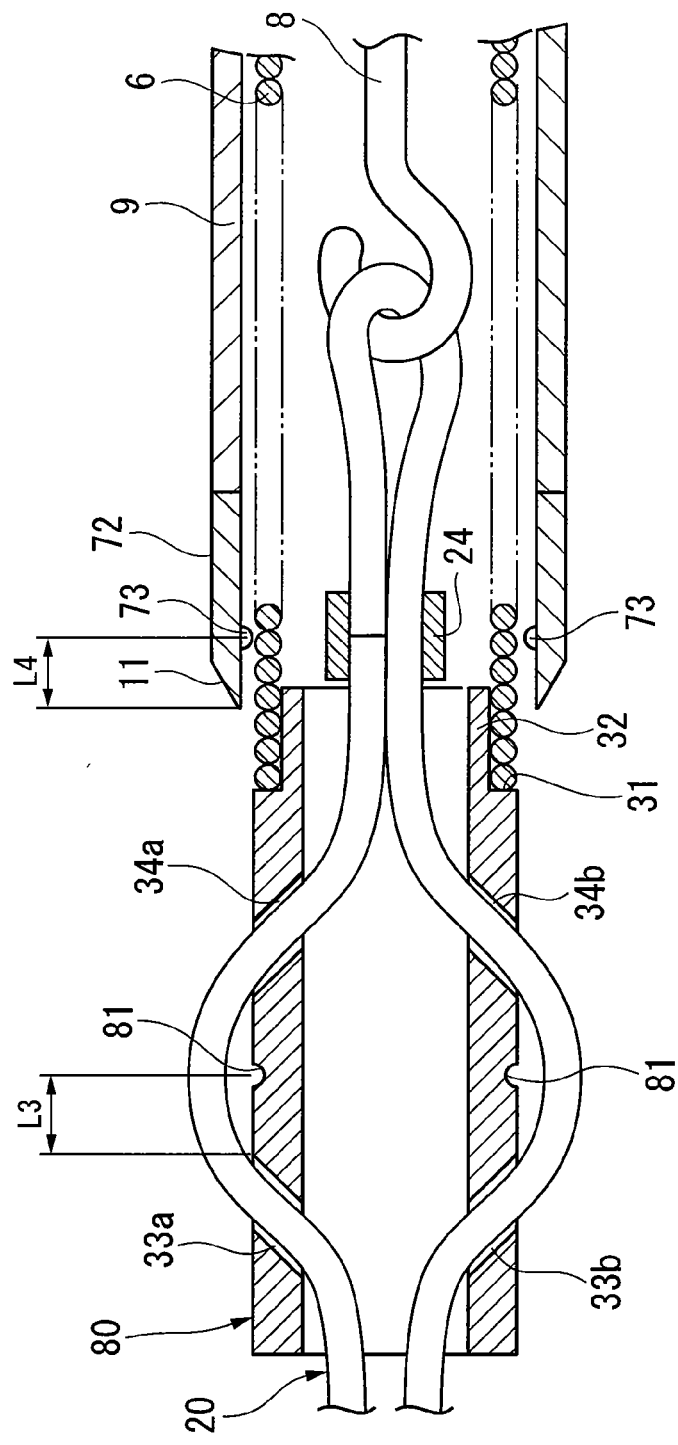
FIG. 14 is an enlarged diagram illustrating a holding member and a cutting member.

Like the holding member 80 shown in FIG. 14, a concave portion 81 may be provided between the distal lateral holes 33a and 33b and the proximal lateral holes 34a and 34b. In this case, it is preferable that a distance L3 from the proximal edge of the distal lateral holes 33a and 33b to the center of the concave portion 81 is smaller than a distance L4 from the distal end of the cutting edge 11 of the cutting member 73 to the center of the protrusions 73. In the holding member 80 and the cutting member 72, since the holding member 80 always engages after the ligature wire 20 is cut, it is necessary to enhance precision in position of the concave portion 81 or the protrusions 73, thereby enhancing the productivity.

Fifth Embodiment

A fifth embodiment of the present invention will be described with reference to FIGS. 15 to 20. The same elements as the first embodiment are denoted by the same reference numerals and repeated descriptions are omitted.

Figure 15:
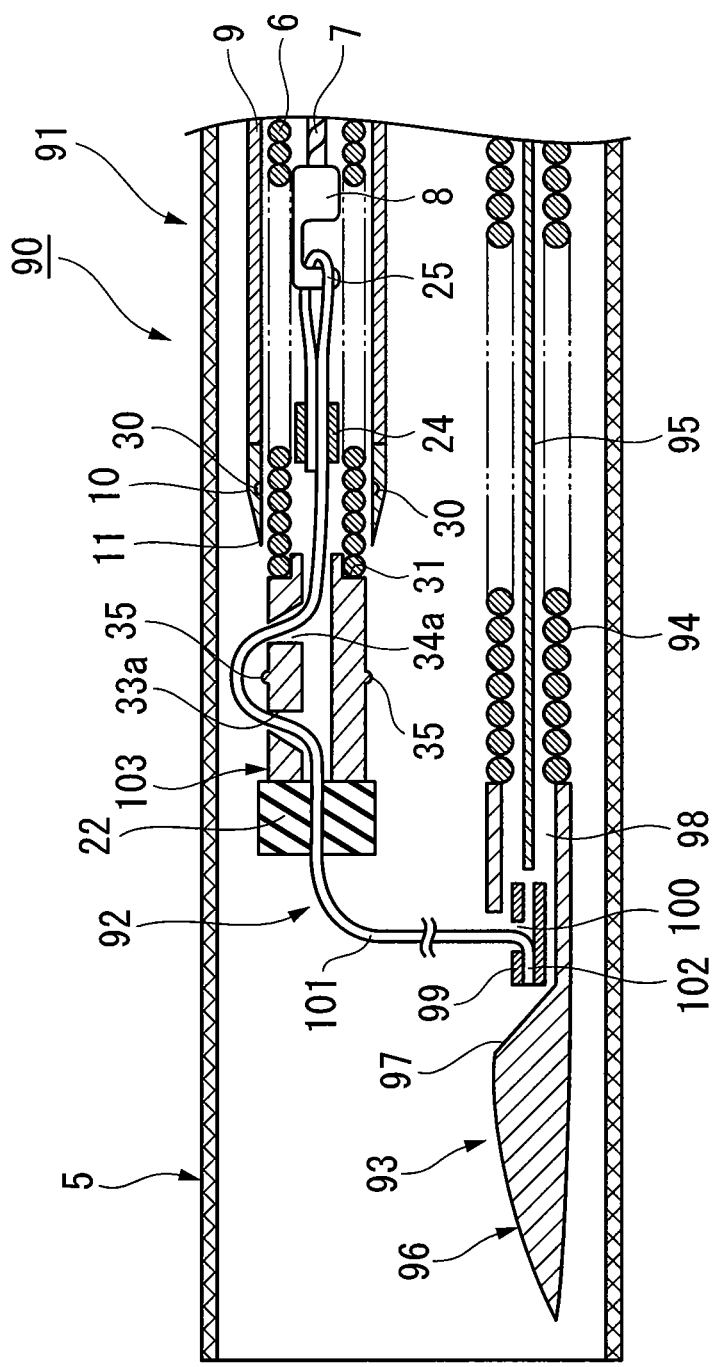
FIG. 15 is a cross-sectional view illustrating a distal end portion of a medical suture instrument according to an embodiment of the invention.

A medical suture and ligature instrument according to this embodiment is a medical suture instrument for suturing a pathological lesion portion to stop bleeding and the like. That is, as shown in FIG. 15, the medical suture instrument 90 includes an operation unit 91 and a medical suture tool (medical suture and ligature tool) 92 mounted on the operation unit 91. In the operation unit 91, an inner sheath 6 and a medical puncture unit 93 having a suture needle as a tissue puncture member are disposed in an outer sheath 5 so as to independently extend and retract. A cutting sheath 9 is disposed on the outer periphery of the inner sheath 6 and an operating wire 7 is inserted through the inner sheath 6.

The medical puncture unit 93 has a flexible puncture portion body 94 formed by winding a metal such as stainless steel in a close coiling shape. The puncture portion body 94 extends along the outer sheath 5 and a flexible extrusion rod 95 is inserted therein so as to extend and retract. The proximal ends of the puncture portion body 94 and the extrusion rod 95 are connected to a handle operating section not shown and can be operated to extend and retract. A needle portion 96 is attached to the distal end of the puncture portion body 94. The needle portion 96 has an acute distal end and extends along the axial line of the puncture portion body 94, and the outer diameter thereof is equal to the outer diameter of the puncture portion body 94. The needle portion 96 is made of a metal material such as stainless steel and an opening 97 is formed in the side surface thereof. A reception portion 98 communicating with the hollow of the puncture portion body 94 is formed in the opening 97 and a separation-preventing tip 99 of the medical suture tool 92 is received therein.

The medical suture tool 92 has a separation-preventing tip 99 as an engaging member and the separation-preventing tip 99 has a pipe shape in which a slit 100 is formed in the longitudinal direction. The slit 100 extends to the substantial center in the longitudinal direction of the separation-preventing tip 99 and a suture thread 101 is inserted therefrom. The suture thread 101 is fixed to the separation-preventing tip 99 by the use of a caulking portion 102 formed to caulk the end portion of the separation-preventing tip 99 and extends by a predetermined length therefrom. The end portion thereof is folded back after passing through a stopper 22 and a holding member 103 so as to form a folding-back portion 25 and is connected to a connecting pipe 24. In the medical suture tool 92, the separation-preventing tip 99 is received in the receiving portion 98 of the needle portion 96 so as to be substantially parallel to the axial line of the puncture portion body 94 and the folding-back portion 25 of the suture thread 101 is locked to the engaging member 8 of the operating wire 7.

Here, the holding member 103 has the same configuration as the holding member 23 of the first embodiment, except that protrusions 35 as the proximal engaging portion are disposed between the distal lateral hole 33a and the proximal lateral hole 34a and one distal lateral hole 33a and one proximal lateral hole 33b are provided. Concave portions 30 engaging with the protrusions 35 are disposed in the inner periphery of the cutting member 10. The holding-side engaging portion and the cutting-side engaging portion may have a combination according to any one of the second to fourth embodiments.

Next, operations of this embodiment will be described.

Figure 16:
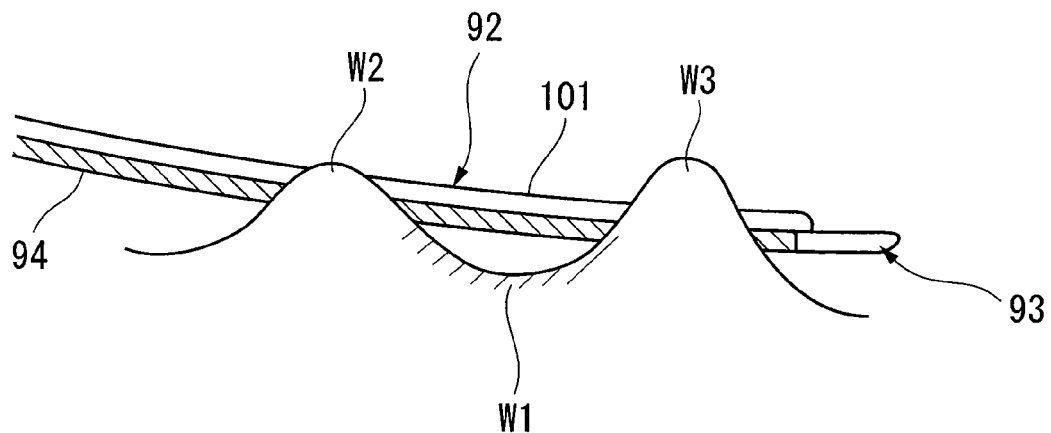
FIG. 16 is a diagram illustrating a state where a biological tissue is punctured with a needle portion of a treatment instrument.

First, the distal end of an endoscope is introduced into the vicinity of a pathological lesion portion W1 to be sutured while observing an image of the endoscope and the medical suture instrument 90 is inserted into a channel of the endoscope. At this time, the inner sheath 6 and the medical puncture unit 93 are received in the outer sheath 5. When it is observed that the outer sheath 5 protrudes from the distal end of the endoscope, the outer sheath 5 is retracted to expose the medical puncture unit 93. Then, By operating the medical puncture unit 93, as shown in FIG. 16, a biological tissue W2 before the pathological lesion portion W1 to stop the bleeding thereof and an opposite biological tissue W3 with the pathological lesion portion W1 interposed therebetween are sequentially punctured with the needle portion 96. Accordingly, the suture thread 101 penetrates the biological tissues W2 and W3 along with the needle portion 96.

Figure 17:
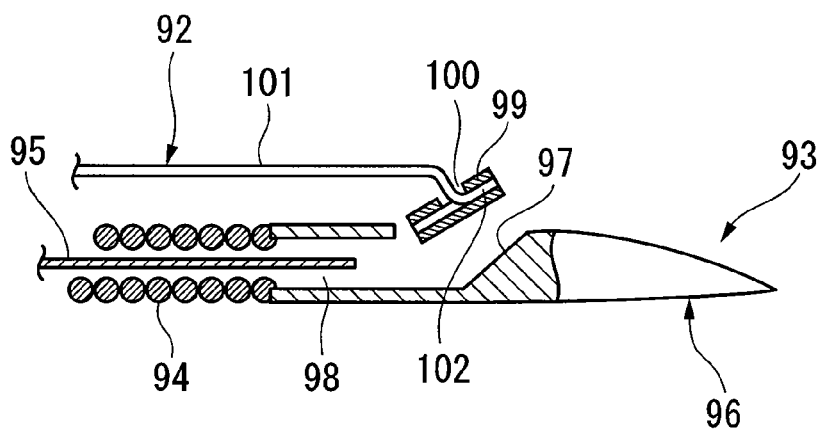
FIG. 17 is a diagram illustrating where a separation-preventing tip of the medical suture tool is pushed out of the needle portion.
Figure 18:
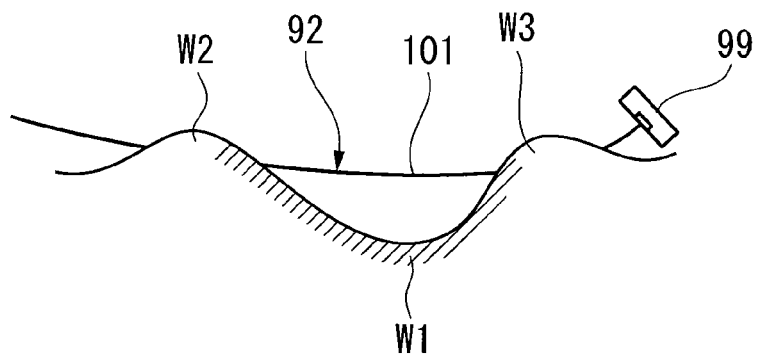
FIG. 18 is a diagram illustrating a state where the needle portion is pulled out of the biological tissue and a suture thread is detained therein.
Figure 19:
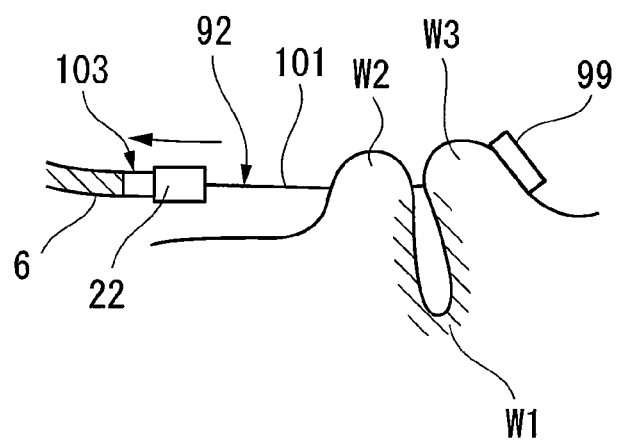
FIG. 19 is a diagram illustrating a procedure of suturing the biological tissue by drawing the suture thread.
Figure 20:
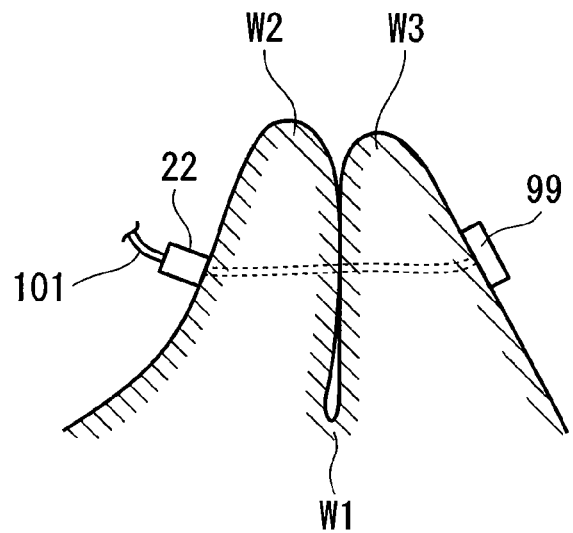
FIG. 20 is a diagram illustrating a state where the biological tissue is sutured with the suture thread.

In this state, as shown in FIG. 17, the extrusion rod 95 is extended and the separation-preventing tip 99 is extruded from the receiving portion 98. Accordingly, the separation-preventing tip 99 is separated from the medical puncture unit 93. Thereafter, when the puncture portion body 94 is retracted, the needle portion 96 is pulled out from the biological tissues W2 and W3. However, as shown in FIG. 18, the separation-preventing tip 99 remains hooked to the biological tissue W3 and the suture thread 101 maintains the state where it penetrates the biological tissues W2 and W3. Then, when the biological tissues W2 and W3 are drawn inward while substantially extruding the stopper 22 by drawing back the operating wire 7, the pathological lesion portion W1 as the bleeding portion is closed and the biological tissues W2 and W3 are sutured as shown in FIG. 19. Thereafter, when the cutting sheath 9 is pushed inward to enter between the proximal lateral hole 34a and the cutting member 10, the proximal side of the suture thread 101 is cut. When the cutting member 10 further advances, the concave portions 30 engage with the protrusions 35, the cutting member 10 is stopped, and the holding member 103 engages the cutting member 10. When the proximal side of the suture thread 101 is cut, the portion of the medical suture tool 92 suturing the biological tissues W2 and W3 is separated from the operation unit 91. In this state, when the endoscope is pulled out, the suture thread 101 suturing the biological tissues W2 and W3 as shown in FIG. 20 is detained in the body. On the other hand, the holding member 103 is discharged out of the body along with the operation unit 91.

Figure 21:
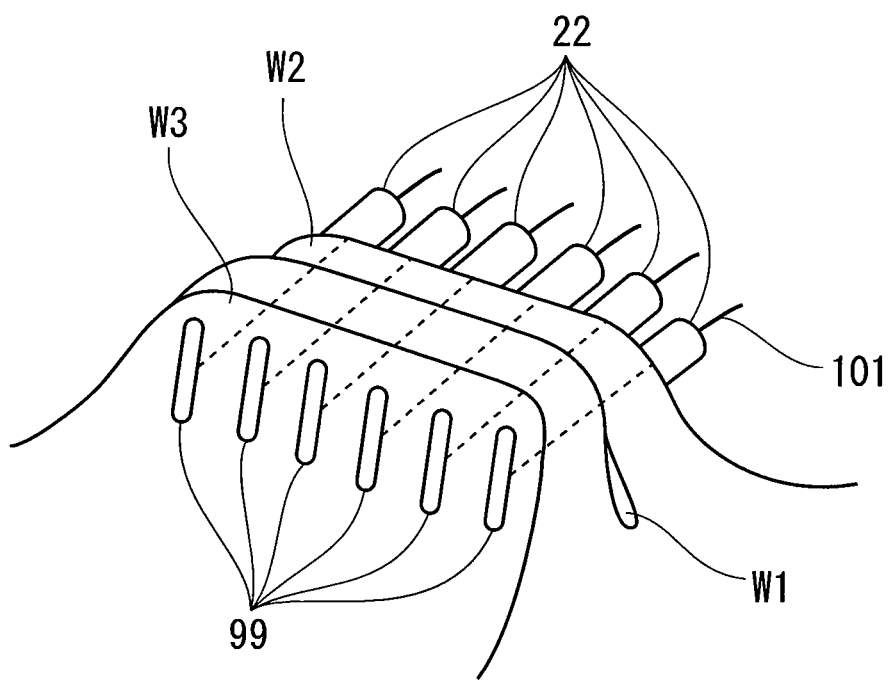
FIG. 21 is a diagram illustrating an example where a biological tissue is sutured by the use of a plurality of medical suture tools.

According to this embodiment, it is possible to suture the biological tissues W2 and W3 by allowing the suture thread 101 to penetrate the biological tissues. Other advantages are equal to those of the first embodiment. Here, since the holding member 103 is removed from the body in a state where it is locked to the operation unit 3, it is possible to suture the biological tissues W2 and W3 by the use of a plurality of suture threads 101. For example, as shown in FIG. 21, it is possible to suture the biological tissues W2 and W3 over a wide range by the use of the plurality of suture threads 101. In this case, since the holding member 103 is reliably separated from one medical suture tool 92 and then a next suture can be performed, the gaps between the neighboring suture threads 101 can be reduced, thereby more reliably suturing the biological tissues W2 and W3.

The invention is not limited to the above-mentioned embodiments, but may be applied widely.

For example, the proximal lateral holes 34a and 34b may be used as the holding-side engaging portions and protrusions engaging the holding-side engaging portions may be disposed on the inner periphery of the cutting member 10.

The holding members 23, 40, 50, 60, 70, 80, and 103 may be provided with only the proximal lateral holes 34a and 34b. In this case, the ligature wire 20 or the suture thread 101 is made to directly pass through the outer periphery of the holding members 23, 40, 50, 60, 70, 80, and 103 from the stopper 22, is drawn into the inside from the proximal lateral holes 34a and 34b, and is drawn out of the opening on the proximal side.

The engaging portions may include a combination of a thin and narrow concave and convex portion in the longitudinal direction. In this case, the cutting member may extend while engaging the holding member and cut the ligature wire 20 or the suture thread 101.

The cutting-side engaging portion according to any one of the first to fifth embodiments may be disposed on the inner periphery of the cutting sheath 9. In this case, the same functions and effects can be obtained.

(Additional Remark 1)

A medical suture and ligature instrument comprising:

an insertion section which is inserted into a body and which has a distal end, a proximal end, and an elongated axis;

a cutting member which is disposed to be movable relative to the insertion section and which has a cutting edge;

a handle operating section which is disposed on the proximal side of the insertion section and which an operator operates;

an operation unit which includes the insertion section, the cutting member, and the handle operating section; and a medical suture and ligature tool which is disposed on the distal side of the operation unit and which sutures or ligatures a biological tissue, wherein the medical suture and ligature tool includes:

a flexible suture and ligature member;

a holding member which has a holding portion for holding the suture and ligature member in a path along which the cutting member moves so as to cut off the suture and ligature member by the use of the cutting member; and a fixing member on which the suture and ligature member is pressed and which fixes the biological tissue in a state where it is sutured or ligatured, and wherein the holding member includes an engaging portion which can engage with the operation unit so as to allow the holding member to engage with the operation unit even after the suture and ligature member is cut by the use of the cutting member.

(Additional Remark 2)

The medical suture and ligature instrument according to Additional Remark 1, wherein a locking member used for locking the suture and ligature member to a biological tissue is attached to a distal end of the suture and ligature member of the medical suture and ligature tool and the operation unit includes a medical puncture unit having a tissue puncture member for puncturing the biological tissue along with the locking member.

(Additional Remark 3)

The medical suture and ligature instrument according to Additional Remark 1, wherein the holding member is provided with a lateral hole for drawing the suture and ligature member into the inside of the holding member from the outside thereof and the engaging portion is disposed so that the cutting member is located closer to the distal end than the lateral hole.

(Additional Remark 4)

The medical suture and ligature instrument according to Additional Remark 1, wherein the cutting member has a cutting edge at the distal end thereof and the holding member is provided with the engaging portion at a position not interfering with the cutting edge.

(Additional Remark 5)

A medical suture and ligature tool comprising:

a flexible suture and ligature member which sutures or ligatures a biological tissue;

a holding member having a holding portion for holding the suture and ligature member in a path along which a cutting member for cutting the suture and ligature member moves; and a fixing member on which the suture and ligature member is pressed and which fixes the biological tissue in a state where it is sutured or ligatured, wherein the holding member includes an engaging portion which can engage with the operation unit so as to allow the holding member to engage with the operation unit even after the suture and ligature member is cut off by the use of the cutting member.

(Additional Remark 6)

The medical suture and ligature instrument according to the third aspect of the invention, wherein the cutting edge and the engaging portion of the holding member are disposed at positions different from each other in a peripheral direction.

(Additional Remark 7)

The medical suture and ligature instrument according to the third aspect of the invention, wherein the engaging portion of the holding member is a concave portion disposed on the outer periphery of the holding member.

(Additional Remark 8)

The medical suture and ligature instrument according to claim 4, wherein the holding member is provided with a lateral hole through which the suture and ligature member to be cut by the use of the cutting edge passes from the outside of the holding member, the cutting member is provided with a cutting-side engaging portion which can engage with the holding-side engaging portion, and a distance from the lateral hole to the holding-side engaging portion is smaller than the distance from the distal end of the cutting member to the cutting-side engaging portion.

The invention claimed is:

1. A medical suture and ligature instrument comprising:
   an insertion section which is inserted into a body and which has a distal end, a proximal end, and an elongated axis;
   a cutting member which has a first engaging portion at an inner periphery surface, a cutting edge, and which is disposed to be movable relative to the insertion section;
   a handle operating section which is disposed on the proximal side of the insertion section and which an operator operates;
   an operation unit which includes the insertion section, the cutting member, and the handle operation section; and
   a medical suture and ligature tool which is disposed on the distal side of the operation unit and which is capable of suturing or ligaturing a biological tissue,
   the medical suture and ligature tool including:
   a flexible suture and ligature member; and
   a holding member which has a holding portion for holding the suture and ligature member in a path along which the cutting member moves so as to cut the suture and ligature member by the use of the cutting member,
   the holding member including a second engaging portion which engages with the cutting member so as to be capable of pulling the holding member out of the body with the operation unit after the cutting member cuts the suture and ligature member.

2. The medical suture and ligature instrument according to claim 1, wherein a locking member used for locking the suture and ligature member to a biological tissue is attached to a distal end of the suture and ligature member of the medical suture and ligature tool and the operation unit includes a medical puncture unit having a tissue puncture member for puncturing the biological tissue along with the locking member.

3. The medical suture and ligature instrument according to claim 1, wherein the holding member is provided with a lateral hole for drawing the suture and ligature member into the holding member from the outside thereof and the second engaging portion is disposed so that the cutting member is located closer to the distal end than the lateral hole.

4. The medical suture and ligature instrument according to claim 1, wherein the cutting member has the cutting edge at the distal end thereof and the holding member is provided with the first engaging portion at a position not interfering with the cutting edge.

5. A medical suture and ligature tool which is used for the medical suture and ligature instrument according to claim 1, the medical suture and ligature tool comprising:
   a flexible suture and ligature member which is capable of suturing or ligaturing a biological tissue; and
   a holding member having a holding portion for holding the suture and ligature member in a path along which a cutting member for cutting the suture and ligature member moves, the holding member including the second engaging portion which engages with the cutting member so as to be capable of pulling the holding member out of the body with the operation unit after the cutting member cuts the suture and ligature member.

6. The medical suture and ligature instrument according to claim 1, wherein the holding member includes a distal lateral hole and a proximal lateral hole penetrating an inner periphery and an outer periphery of holding member,
   the distal lateral hole is disposed in a distal side of the second engaging portion and lets the suture and ligature member into the inner periphery of the holding member from the outer periphery of the holding member, and
   the proximal lateral hole is disposed in proximal side of the second engaging portion and lets the suture and ligature member into the inner periphery of the holding member from the outer periphery of the holding member.

7. The medical suture and ligature instrument according to claim 6, wherein the second engaging portion includes a protrusion,
   the cutting member includes a concave portion configuring the first engaging portion which engage with the protrusion, and the distance from the distal end of the cutting edge to the concave portion is shorter than the distance from the protrusion to the proximal peripheral edge of the distal lateral hole.

8. The medical suture and ligature instrument according to claim 7, wherein the protrusion has a triangular wedge shape in side view, the proximal side of the protrusion has a slope, and the distal side of the protrusion has a plane perpendicular to the axial direction.

9. The medical suture and ligature instrument according to claim 6, wherein the second engaging portion includes a tapered portion, and
   in a side sectional view, the tapered portion is disposed between the distal lateral hole and the proximal lateral hole, and extends outward in the diameter direction and toward the proximal end from the distal lateral hole and is bent at an angle greater than or equal to 90 degrees, and reaches the position of the proximal lateral hole while forming a slope.

10. The medical suture and ligature instrument according to claim 6, wherein the second engaging portion includes a protrusion disposed at a position displaced in the peripheral direction from the position of the proximal lateral hole, the cutting edge is divided into two portions by notching two positions in the peripheral direction, and a guide portion for receiving the protrusion is provided at the notched portion of the cutting edge.

11. The medical suture and ligature instrument according to claim 6, wherein the second engaging portion includes a concave portion,
the cutting member includes a protrusion configuring the first engaging portion which engages with the concave portion, and the distance from the distal end of the cutting edge to the protrusion is larger than the distance from the proximal edge of the proximal lateral hole to the concave portions.

12. The medical suture and ligature instrument according to claim 6, wherein the second engaging portion includes a concave portion that is provided between the distal lateral hole and the proximal lateral hole, the cutting member includes a protrusion configuring the first engaging portion which engages with the concave portion, and the distance from the proximal edge of the distal lateral hole to the center of the concave portion is smaller than the distance from the distal end of the cutting edge to the center of the protrusions.

13. The medical suture and ligature instrument according to claim 1, wherein the operation unit includes a medical puncture unit, the medical puncture unit comprises:

a puncture portion body;

a flexible extrusion rod inserted to the puncture portion body so as to extend and retract; and a needle portion which is attached to the distal end of the puncture portion body;

wherein an opening is formed in the side surface of the needle portion, and the opening receives an engaging member, which is fixed to the suture and ligature member.

* * * * *